US008198300B2

(12) United States Patent
Maccioni et al.

(10) Patent No.: US 8,198,300 B2
(45) Date of Patent: Jun. 12, 2012

(54) **METHOD FOR PREVENTING *TAU* PROTEIN AGGREGATION AND TREATING ALZHEIMER'S DISEASE WITH A QUINOLINE DERIVATIVE COMPOUND**

(75) Inventors: Ricardo B. Maccioni, Santiago (CL); Leonardo P Navarrete, Santiago (CL); Aurelio San Martin, Santiago (CL)

(73) Assignee: Universidad De Chile, Santiago (CL)

( * ) Notice: Subject to any disclaimer, the term of this patent is extended or adjusted under 35 U.S.C. 154(b) by 0 days.

(21) Appl. No.: 12/770,284

(22) Filed: Apr. 29, 2010

(65) Prior Publication Data
US 2011/0269793 A1 Nov. 3, 2011

(51) Int. Cl.
*A61K 31/47* (2006.01)
*A61P 25/28* (2006.01)
*C07D 215/12* (2006.01)
(52) U.S. Cl. ..................... 514/311; 546/173
(58) Field of Classification Search ............ None
See application file for complete search history.

(56) References Cited

U.S. PATENT DOCUMENTS
2005/0009865 A1* 1/2005 Kudo et al. .......... 514/311

OTHER PUBLICATIONS

Jesus Avila, et al; "Role of Tau Protein in Both Physiological and Pathological Conditions", Physiol. Rev. 84: 361-384, Apr. 2004; 10.1152/physrev.0024.2003; www.prv.org.
J.Kevin Baird, et al; "Treatment of Chloroquine-Resistant Plasmodium *vivax* with Chloroquine and Primaquine or Halofantrine", JID 1995, June; pp. 1678-1682, Downloaded from jid.oxfordjournals.org at Universidad de Chile-Casilla Choice on Jan. 31, 2011.
Simon F. Campbell, et al; "2,4-Diamino-6,7-dimethoxyquinoline Derivatives as $\alpha_1$-Adrenoceptor Antagonists and Antihypertensive Agents", Journal of Medicinal Chemistry, 1988, vol. 31, No. 5, pp. 1031-1035.
Roland Brandt, et al; "Interaction of Tau with the Neutral Plasma Membrane Mediated by Tau's Amino-terminal Projection Domain", The Journal of Cell Biology, vol. 131, No. 5, Dec. 1995, pp. 1327-1340.
Daniel Cross, et al; "A tau-like protein interacts with stress fibers and microtubules in human and rodent cultured cell lines", Journal of Cell Science 105, 51-60, 1993.
Jeffrey L. Cummings, M.D.; "Alzheimer's Disease", Review Article, The New England Journal of Medicine, 351;1, Jul. 1, 2004, pp. 56-67.
Gustavo A. Farias, et al; "Tubulin, Actin, and Tau Protein Interactions and the Study of Their Macromolecular Assemblies", Journal of Cellular Biochemistry 85:315-324 (2002).
Jorge A. Fernandez, et al; "The Damage Signals Hypothesis of Alzheimer's Disease Pathogenesis", Journal of Alzheimer's Disease 14 (2008), pp. 329-333.
Adriana Ferreira, et al; "Estrogen-Enhanced Neurite Growth: Evidence for a Selective Induction of Tau and Stable Microtubules", The Journal of Neuroscience, Feb. 1991, 11(2): pp. 392-400.

Peter Friedhoff, et al.; "Rapid Assembly of Alzheimer-like Paired Helical Filaments from Microtubule-Associated Protein Tau Monitored by Fluorescence in Solution", Biochemistry 1998, 37, pp. 10223-10230.
Ehud Gazit; "A possible role for π-stacking in the self-assembly of amyloid fibrils", FASEB J. 16: 77-83.
Charles G. Glabe; "Conformation-dependent antibodies target diseases of protein misfolding", Trends in Biochemical Sciences, vol. 29, No. 10, Oct. 2004, pp. 542-547.
Michel Goedert; "Tau protein and neurodegeneration", Seminars in Cell & Developmental Biology 15 (2004), pp. 45-49.
Robert C. Green, MD, MPH, et al; "Risk of Dementia Among White and African American Relatives of Patients With Alzheimer Disease" JAMA, vol. 287, No. 3, pp. 329-336, Jan. 16, 2002(Reprinted).
Paula Hernandez, et al; "Tau Phosphorylation by cdk5 and Fyn in Response to Amyloid Peptide $A\beta_{25-35}$ : Involvement of Lipid Rafts", Journal of Alzheimer's Disease 16 (2009) 149-156, DOI 10.3233/JAD-2009-0933.
Christopher A. Hunter, et al; "The Nature of π-π Interactions", J. Am. Chem. Soc. 1990, 112, 5525-5534.
Hideyo Inouye, et al; "Structure of Core Domain of Fibril-Forming PHF/Tau Fragments", Biophysical Journal, vol. 90, Mar. 2006, 1774-1789.
Ross Jakes, et al; "Identification of 3- and 4-repeat tau isoforms within the PHF in Alzheimer's disease", The EMBO Journal, vol. 10, No. 10, pp. 2725-2729, 1991.
Jean-Charles Lambert, et al; "A new polymorphism in the APOE promoter associated with risk of developing Alzheimer's Disease", Human Molecular Genetics, 1998, vol. 7, No. 3, pp. 533-540.
Cristobál Maccioni, et al; "New paradigms in the study of the pathogenesis of Alzheimers disease", Rev. chil. Neuron-psiquiatr. V.41 supl.2 Santiago Nov. 2003, pp. 1-11.
Ricardo B. Maccioni, et al; "Differential interaction of synthetic peptides from the carboxyl-terminal regulatory domain of tubulin with microtubule-associated proteins", The EMBO Journal, vol. 7, No. 7, pp. 1957-1963, 1988.
Ricardo B. Maccioni, et al; "The Role of Neuroimmunomodulation in Alzheimer's Disease", Neuroimmunomodulation: Ann. N.Y. Acad. Sci. 1153; 240-246 (2009), doi: 10.111/j.1749-6632.2008.03972.x.
O. Sumner Makin, et al; "Molecular basis for amyloid fibril formation and stability", PNAS, Jan. 11, 2005, vol. 102, No. 2, pp. 315-320.
Mark P. Mattson; "Pathways towards and away from Alzheimer's disease", Nature, vol, 430, Aug. 5, 2004, www.nature.com/nature, pp. 631-639, & 107.

(Continued)

*Primary Examiner* — Janet Andres
*Assistant Examiner* — Timothy R Rozof
(74) *Attorney, Agent, or Firm* — Ladas & Parry LLP

(57) ABSTRACT

Method for the prevention of the tau protein aggregation and treating Alzheimer's disease by administering a quinoline derivative compound of formula

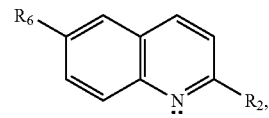

wherein $R_2$ is 2-(4-aminophenyl) or 2-(4-methylphenyl) and $R_6$ is methyl as an inhibitor of the tau protein aggregation.

1 Claim, 9 Drawing Sheets

OTHER PUBLICATIONS

Nobuyuki Okamura, et al; "Quinoline and Benzimidazole Derivatives: Candidate Probes for In Vivo Imaging of Tau Pathology in Alzheimer's Disease", The Journal of Neuroscience, Nov. 23, 2005-25(47):10857-10862.

Gabriela Paglini, et al; "Evidence for the Participation of the Neuron-Specific CDK5 Activator P35 during Laminin-Enhanced Axonal Growth", The Journal of Neuroscience, Dec. 1, 1998, 18(23):9858-9869.

Marcus Pickhardt, et al; "Anthraquinones Inhibit Tau Aggregation and Dissolve Alzheimer's Paired Helical Filaments in Vitro and in Cells", The Journal of Biological Chemistry, vol. 280, No. 5, Issue of Feb. 4, pp. 3628-3635, 2005; paper available online at http://www.jbc.org.

Carolyn A. Rankin, et al; "Tau phosphorylation of GSK-3β promotes tangle-like filament morphology", Published Jun. 28, 2007, Molecular Neurodegeneration 2007, 2:12; doi:10.1186/1750-1326-2-12, 14 pages.

C. Hugh Reynolds, et al; "Phosphorylation Sites on Tau Identified by Nanoelectrospray Mass Spectrometry: Differences In Vitro Between the Mitogen-Activated Protein Kinases ERK2, c-Jun N-Terminal Kinase and P38, and Glycogen Synthase Kinase-3β", Journal of Neurochemistry, 74, 1587-1595 (2000).

Alex E. Roher‡§, et al; "Morphology and Toxicity of Aβ-(1-42) Dimer Derived from Neuritic and Vascular Amyloid Deposits of Alzheimer's Disease", The Journal of Biological Chemistry, vol. 271, No. 34, Issue of Aug. 23, pp. 20631-20635, 1996.

Leonel E. Rojo, [a,d] et al; "Neuroinflammation: Implications for the Pathogenesis and Molecular Diagnosis of Alzheimer's Disease", Archives of Medical Research 39 (2008) 1-16.

Mark M. Black, et al; "Tau Is Enriched on Dynamic Microtubules in the Distal Region of Growing Axons", The Journal of Neuroscience, Jun. 1, 1996, 16(11):3601-3619.

Martin Von Bergen, et al; "Tau aggregation is driven by a transition from random coil to beta sheet structure", Biochimica et Biophysica Acta 1739 (2005) 158-166, Available online at www.sciencedirect.com.

Robin V. Ward, et al; "Fractionation and characterization of oligomeric, protofibrillar and fibrillar forms of β-amyloid peptide", Biochem. J. (2000) 348, 137-144.

Cristian A. Zambrano, etl al; "Oxidative Stress Promotes $_T$ Dephosphorylation In Neuronal Cells: The Roles of Cdk5 and PP1", Free Radical Biology & Medicine, vol. 36, No. 11, pp. 1393-1402, 2004, doi:10.1016/j.freeradbiomed.2004.03.007.

Wan-Kyng Liu, et al; "Abnormal Tau Proteins from Alzheimer's Disease Brains Purification and Amino Acid Analysis", The Journal of Biological Chemistry, vol. 266, No. 32, Issue of Nov. 15, pp. 21723-21727, 1991.

Jozef Sevcik, et al; "X-ray structure of the PHF core C-terminus: Insight into the folding of the intrinsically disordered protein tau in Alzheimer's disease", FEBS Letters 581 (2007) 5872-5878.

M. Pevalova, et al; "Post-translational modifications of tau protein", Bratisl Lek Listy 2006; 107(0-10): 346-353.

Naveena Yanamala, et al; "Preferential binding of allosteric modulators to active and inactive conformational states of metabotropic glutamate receptors", from Sixth International Conference on Bioinformatics (InCoB2007) Hong Kong, Aug. 27-30, 2007, Published Feb. 13, 2008, BMC Bioinformatics 2008, 9(Suppl) 1:S16, doi:10.1186/1471-2105-9-S1-S16.

R.O. Kuljis, et al; Tomographic Visualization of Cholinesterase, Ann. Neurol. 60(6): 2006, 745-6.

Robert G. Ridley, "Medical need, scientific opportunity and the drive for antimalarial drugs", Nature, vol. 415, Feb. 7, 2002, pp. 686-693.

M.P. Sanchez, et al; "La proteina tau en enfermedades neurodegenerativas. Taupatias", Revista de Neurologia. 2001, 33(2):169-177.

Luis Astudillo Saavedra, et al; "Synthesis of New Diversely Linked Biquinoline Derivatives by Multicomponent Imino-Diels-Alder Cycloaddition and Intramolecular Friedel-Crafts Cyclization", Synthesis 2010, No. 4, pp. 0593-0600, Advanced online publication Dec. 16, 2009.

Win-Long Chia, et al; "Synthesis and mesomorphic properties on the series of 2-(4-alkylphenyl)-6-methylquinolines and 2-(4-alkoxyphenyl)-6-methylquinolines", Liquid Crystals, vol. 36, No. 5, May 2009, pp. 557-563.

G.Y.Paris, et al; "Anthelmintie Quaternary Salts, V. 2-(p-Dialkylaminophenyl)-1-methylquinolinium Salts", J. Med Chem. Jan. 1970, vol. 13, No. 1, pp. 122-124.

Vladimir V. Kouznetsov, et al; "Recent Progress in the Synthesis of Quinolines", Current Organic Chemistry, vol. 9, Issue 2, pp. 141-161; Jan. 2005.

* cited by examiner

Scatchard saturation test for
heparin induced tau filaments

METHOD FOR PREVENTING TAU PROTEIN AGGREGATION AND TREATING ALZHEIMER'S DISEASE WITH A QUINOLINE DERIVATIVE COMPOUND

FIELD OF THE INVENTION

The present invention refers to specific quinoline molecules, polymerized tau binding ligands, as potential blockers of the tau aggregation before the formation of NFTs. Said quinolines preferably present an amine group or a methyl group in a meta position of the nitrogenated ring, and show the highest disaggregating activity of tau polymers, and thereby are useful in the treatment of Alzheimer's disease. The present invention provides quinoline compounds that prevent the formation and at the same time disaggregate the NTFs, therefore being useful in the treatment and prophylaxis of the Alzheimer's disease.

PREVIOUS ART

The Alzheimer's disease (AD) is a neurodegenerative disorder, that evolves slowly, and the most common cause of dementia, primarily affecting 2% of the less than 65 years old population and almost 50% of the 85 or more years old population. Consequently, there is an urgency for treatment, in order to avoid a serious epidemiological process that could be unleashed in the next decade if such a treatment is not found (Green R. C., Cupples L. A., Go R., Benke K. S., Edeki T., Griffith P. A., Williams M., Hipps Y., Graff-Radford N., Bachman D., Farrer L. A. (2002), MIRAGE Study Group, Risk of dementia among white and African American relatives of patients with Alzheimer disease, JAMA 287 (3): 329-36; Maccioni R. B., Lavados M., Maccioni C. B. and Mendoza A. (2004), Biological markers of Alzheimer's disease and mild cognitive impairment, Current Alzheimer Research 1: 307-314; Maccioni R. B., Farias G. A., Rojo L. E., Sekler M. A. and Kuljis R. O. (2008), What have we learned from the tau hypothesis, In: Hypotheses and Research Milestones in Alzheimer's Disease (R. B. Maccioni & G. Perry, eds.), Springer-Verlag, New York-Heidelberg). EA is also one of the primary public health problems because it is one of the disorders that carries the biggest economic impact in modern society. (Wimp A., Winblad B. (2001), Health economical aspects of Alzheimer disease and its treatment, Psychogeriatrics. 1: 189-93; Winblad B. (2001), Maintaining functional and behavioral abilities in Alzheimer disease, Alzheimer Dis. Assoc. Disord 1: S34-40). The AD is considered as a consistent clinical-pathological entity in the association of a slowly progressing dementia, the beginning of the old age, and the neuronal loss and the presence of senile or neuritic plaques (SP) and neurofibrillary tangles (NFTs) that can be observed in the cortex, in concentrations that are clearly higher than those that would normally be expected due to physiological ageing (Maccioni, R. B., Barbeito L., and Muñoz J. P. (2001), The molecular bases of Alzheimer's disease and other neurodegenerative disorders, Arch. Medical Research, 32: 367-381; Rojo L. E., Fernández J. A., Maccioni A. A., Jimenez J. M., Maccioni R. B. (2008), Neuroinflammation: implications for the pathogenesis and molecular diagnosis of Alzheimer's disease, Arch. Med. Res. 39(1):1-16). As a result of the synapse degeneration and of neuronal death, certain regions of the brain such as the frontal and temporal lobe, the last one being involved in learning and memory processes, are affected and present a reduced size in AD patients as is clearly demonstrated by Mattson M. (2004), Pathways towards and away from Alzheimer disease, Nature 430 (7000): 631-9. Since there are other types of dementia of different etiology such as for example of vascular origin, due to B12 vitamin deficit, neurodegenerative (such as front-temporal dementia) and infectious (including syphilis, HIV associated dementia and Creutzfeld-Jakob), among others (Mc Khann G. M. (1991), The future of child neurology, J. Child Neurol. 6 (2):167-72), the differential and certainty diagnosis of DA still requires a post-mortem neuro-pathological analysis (Kuljis R. O., Darvesh S., Greig N. H., Geula C. (2006), Tomographic visualization of cholinesterase, Ann. Neurol. 60(6): 745-6). This consists in the histological analysis of sections from the brain tissue that must present a sufficient number of co-existing SP and NFTs in particular brain zones such as the hippocampus and the Meynert nucleus. The diagnose is based in clinical criteria and neuro physical examinations, the identification of the disease typical symptoms and the exclusion of other dementia causes (Dubois B., Feldman H., Jacova C. (2007), Research criteria for the diagnosis of Alzheimer's disease: revising the NINCDS-ADRDA criteria, Lancet Neurol. 6: 734-46). In this respect it can be emphasized that the lack of a high confidence level certainty bio marker has, on one hand, delayed the study of AD, and on the other it has made more difficult the early diagnosis of this pathology.

Clinically, AD is characterized by a progressive deterioration and decrease in the cognitive functions, such as language memory and visual space orientation. The AD is further characterized by a gradual memory loss, decrease in the capacity to work out routine tasks, space and time disorientation, learning difficulties, loss of linguistic capacity, reasoning deterioration, rapid mood changes and personality alterations (Katzman R. (2004), Luigi Amaducci memorial award winner's paper 2003, A neurologist's view of Alzheimer's disease and dementia, Int Psychogeriatr. 16 (3): 259-73). In its initial stage a neuron loss is not observed, but a neuron dysfunction, that gradually increases to more severe stages in which a severe cognitive deterioration is observed, associated to neuronal loss in the hippocampus area, the entorhinal cortex and then in the pre-frontal and temporal cortex as is clearly demonstrated in M. (2004), Pathways towards and away from Alzheimer disease, Nature, 430 (7000): 631-9.

AD is related with a wide and gradual neuronal loss, but the main neuro-pathological event consists in the deposition of SP and NTFs. The SP are formed mainly of the Aβ (1-42) variant (Mattson M. (2004), Pathways towards and away from Alzheimer disease, Nature 430 (7000): 631-9). In the case of NFTs, they are comprised of a protein associated to the neuronal cytoskeleton known as tau, that is hyperphosphorylated in the AD patients brains (Kurt M. A., Davies D. C., Kidd M. (1997), Paired helical filament morphology varies with intracellular location in Alzheimer's disease brain, Neurosc. Lett. 239 (1): 41-4; Maccioni, R. B., Barbeito L., and Munoz J. P. (2001), The molecular bases of Alzheimer's disease and other neurodegenerative disorders, Arch. Medical Research 32: 367-381; Maccioni R. B., Lavados M., Maccioni C. B. and Mendoza A. (2004), Biological markers of Alzheimer's disease and mild cognitive impairment, Current Alzheimer Research 1: 307-314). By means of unknown mechanisms, tau undergoes important transformations, such as abnormal phosphorylation due to the deregulated activity of various kinases and phosphatases that affect its normal biological function (Zambrano C. A., Egaña J. T., Núñez M. T., Maccioni R. B., González-Billault C. (2004), Oxidative stress promotes tau dephosphorylation in neuronal cells: the roles of cdk5 and PP1, Free Radic. Biol. Med. 36 (11): 1393-402). Under these circumstances, tau starts to aggregate, originating the NTFs, structures that constitute a characteristic histopathological marker of EA along with the SP (Maccioni C., Arzola M. E., Mujica L. and Maccioni R. B. (2003), New paradigms in the study of the pathogenesis of the Alzheimer's disease, Rev. Chil. Neuro-Psiquiatr. 41 (2): 33-46). SP and NTFs are mainly present in brain regions involved in learning, memory and emotional conduct, such as hippocampus, cerebral cortex and tonsil.

As for its pathogenesis, it is clear that the characteristic lesions of EA, i.e., the NFTs and the senile plaques (SP), are not the triggering events of its pathogenesis, but the late result of processes that happen during many years. Different hypothesis have been proposed about AD, but recently the AD unification theory has found greater acceptance (Fernández J. A., Rojo L., Kuljis R. and Maccioni R. B. (2008), "The damage signals hypothesis of Alzheimer's disease pathogenesis", J. Alzheimer Dis. 14: 329-33; Maccioni R. B., Rojo L., Fernández J. and Kuljis R. O. (2008), "Neuroimmunomodulation in Alzheimer's disease", Ann. N.Y. Acad. Sci.), that suggests that there are a series of injury-alarm signals in the innate immune system, in the early stages of the AD pathogenesis. Endogenous injury damage signals such as Aβ oligomers, LDL oxydase, free radicals, mechanic injury and advanced glycosylation products (AGEs), provided by external factors like traumatism, high fat intake, Vitamin B deficit, infections and iron overload among others, activate the microglia by means of the AGEs receptors. Separately, LDL-oxydases activate toll type receptors (TLRs), in particular TLR4. Additional injury signals such as traumatism and free radicals possibly act in separate receptors as described in Fernández J. A., Rojo L., Kuljis R. and Maccioni R. B. (2008), "The damage signals hypothesis of Alzheimer's disease pathogenesis", J. Alzheimer Dis. 14: 329-33; Maccioni R. B., Farias G. A., Rojo L. E., Sekler M. A. and Kuljis R. O. (2008), What have we learned from the tau hypothesis, In: Hypotheses and Research Milestones in Alzheimer's Disease (R. B. Maccioni & G. Perry, Eds.), Springer-Verlag, New York-Heidelberg. Separately and in various combinations, these signals could trigger alarm mechanisms in the innate immune system, resulting in an increase of the NFκ-B levels, a transcription factor that would increase the expression of the pro inflammation cytokine genes (TNF-α, IL-1β, IL-6) released by the microglia and that promote misguided signal cascades in the affected neurons (Rojo L. E., Fernandez J. A., Maccioni A. A., Jimenez J. M., Maccioni R. B. (2008), Neuroinflammation: implications for the pathogenesis and molecular diagnosis of Alzheimer's disease, Arch. Med. Res. 39 (1): 1-16). In this way, the levels of these cytokines are increased in the cerebrospinal fluid (LCR). These signals would be directly related with the neuronal injury, due to the activation of cellular cycle enzymes such as cdk-5, which can be seen in alterations like hyperphosphorylation of the tau protein and in the formation of paired helical filaments (PHFs), processes that result in a neuronal degeneration and progressively severe clinical manifestations that affect cognitive and conduct processes (Fernández J. A., Rojo L., Kuljis R. and Maccioni R. B. (2008), "The damage signals hypothesis of Alzheimer's disease pathogenesis", J. Alzheimer Dis. 14: 329-33). Senile plaques (SP) are structures located in the extra-cellular space where the nervous terminals move, and comprise small deposits of fibrils and β-amyloid (Aβ) amorphous aggregates (Liu W. K., Ksiezak-Reding H., Yen S. H. (1991), Abnormal tau proteins from Alzheimer's disease brains, Purification and amino acid analysis, J. Biol. Chem. 266 (32): 21723-7). They consist of annular conglomerates of degenerated bodies and neuronal prolongations around a central deposit of Aβ peptide having a variable length of 39-43 amino acids. These peptide derives from the proteolytic processing of the amyloid precursor protein (APP) (Glenner G. G., Wong C. W., Quaranta V., Eanes E. D. (1984), The amyloid deposits in Alzheimer's disease: their nature and pathogenesis, Appl. Pathol. 2 (6): 357-69).

Three enzymes are responsible of this process. The APP can be fragmented by the combined action of α-secretase, followed by the action of γ-secretase, generating various soluble APP fragments. However, when the action over APP is first carried out by the β-secretase followed by the action of γ-secretase, the fragments Aβ-1-40 and Aβ 1-92 are released, initiating the amyloidogenic path, the latter fragment of which has the largest capacity of auto-aggregation (Hardy J. (1997), Amyloid, the presenilins and Alzheimer's disease, Trends Neurosci. 20 (4): 154-9).

The presence of Aβ extra-cellular plaques is a central fact in the neuropathology of EA. The β-amyloid theory (Cummings J. L. (2004), Alzheimer's disease, N. Engl. J. Med. 351 (1): 56-67), is based in the fact that the Aβ-aggregates are the triggering factor of a multitude of neurotoxic paths among which the excitotoxicity, alterations of the calcium homeostasis, massive free radical production and neuroinflammatory processes can be included. On the other hand, there are various studies that suggest that small peptide oligomers can be the toxic form (Roher A. E., Chaney M. O., Kuo Y. M., Webster S. D., Stine W. B., Haverkamp L. J., Woods A. S., Cotter R. J., Tuohy J. M., Krafft G. A., Bonnell B. S., Emmerling M. R. (1996), Morphology and toxicity of Abeta-(1-42) dimer derived from neuritic and vascular amyloid deposits of Alzheimer's disease, J. Biol. Chem. 271 (34): 20631-5; Lambert J. C., Pasquier F., Cottel D., Frigard B., Amouyel P., Chartier-Harlin M. C. (1998), A new polymorphism in the APOE promoter associated with risk of developing Alzheimer's disease, Hum. Mol. Genet. (3): 533-40).

Several studies have demonstrated that SP are found both in AD brains and in normal senile controls as long as it matters old people, thus suggesting that the plaques could be senile markers more that dementia markers (Maccioni R. B., Farias G. A., Rojo L. E., Sekler M. A. and Kuljis R. O. (2008), What have we learned from the tau hypothesis, In: Hypotheses and Research Milestones in Alzheimer's Disease (R. B. Maccioni & G. Perry, Eds.), Springer-Verlag, New York-Heidelberg). Consequently, the formation of amyloid components is common in normal ageing, and therefore the Aβ possibly precedes the NFTs formation; but the presence of both key cellular events is needed in AD to complementary lead to the loss of activity of the affected neurons (Maccioni, R. B., Barbeito L., and Muñoz J. P. (2001), The molecular bases of Alzheimer's disease and other neurodegenerative disorders, Arch. Medical Research. 32: 367-381).

The tau protein is a protein that is normally found associated to the microtubules, and has an important function in their assembling, such as the stabilization of the microtubules against the dynamic instability and the linking of the microtubules to other filaments of the cytoskeleton (Maccioni R. B. and Cambiazo V. (1995), Role of microtubule-associated proteins in the control of microtubule assembly, Physiol. Rev. (4): 835-864; Maccioni, R. B., Barbeito L., and Muñoz J. P. (2001), The molecular bases of Alzheimer's disease and other neurodegenerative disorders, Arch. Medical Research 32: 367-381). The tau protein is a part of the MAPs or Microtubules Associated Proteins. In humans, it is found almost exclusively in neurons (Maccioni R. B. and Arechaga J. (1987), "The Cytoskeleton in Cell Differentiation and Development", Oxford University Press, U.K. 367 pp; Maccioni R. B. and Cambiazo V. (1995), Role of microtubule-associated proteins in the control of microtubule assembly, Physiol. Rev. 75 (4): 835-864) and presents itself in 6 isoforms, that derive from the expression of only one gene. This gene is found in the long arm of chromosome 17, in position 21 (17q21) and has 13 exons, which by an alternative cut and splice process generate 6 molecular isoforms, having between 352 and 441 amino acids (Goedert M. (2004). Tau protein and neurodegeneration, Seminars in Cell & Developmental Biology 15:45-49).

The scheme proposed in Goedert M. (2004), Tau protein and neurodegeneration, Seminars in Cell & Developmental Biology 15: 45-49, summarizes the information about the structure of the tau gene and its expression by the means of alternative splicing in six isoforms in the human brain. As a result of this process, 6 isoforms from 45 kDa to 65 kDa are generated, which are differentially expressed during the development and can be found as well distributed in different neuronal sub-populations (Kosik K. S., Orecchio L. D., Bakalis S., Neve R. L. (1989), Developmentally regulated expression of specific tau sequences, Neuron. 2 (4): 1389-97).

The N-terminus region of the tau protein has a variable length, depending on the fact that the isoform presents or not the exons 2 and/or 3. This region is known as the projection domain, because once the tau protein interacts with the microtubules it projects itself from them to the outside. By means of this projection tau can interact with other elements of the cytoskeleton such as actin or spectrin filaments (Cross D., Vial C. and Maccioni R. B. (1993), A tau-like protein interacts with stress fibers and microtubules inhuman and rodent cell lines, J. Cell. Sci. 105: 51-60; Farias G. A., Munoz J. P., Garrido J., Maccioni R. B. Tubulin, actin, and tau protein interactions and the study of their macromolecular assemblies, (2002) J. Cell Biochem. 85: 315-324; Carlier M. F., Simon C., Cassoly R., Pradel L. A. (1984), Interaction between microtubule-associated protein tau and spectrin, Biochimie. 66: 305-311) or interact with the plasmatic membrane (Brandt R., Leger J., Lee G. (1995), Interaction of tau with neural plasma membrane mediated by tau's aminoterminal projection domain, J Cell Biol. 131: 1327-1340; Hernández P., Lee G., Sjoberg M. and Maccioni R. B. (2008), "Tau phosphorylation by cdk5 and Fyn in response to amyloid peptide Aβ 25-35: involvement of lipid rafts", J. Alz. Dis. (In press))

On the other hand, in the C-terminus domain are located the repetitive sequence domains, in "tandem", that are involved in the binding to microtubules (Maccioni R. B. and Arechaga J. (1987), "The Cytoskeleton in Cell Differentiation and Development", Oxford University Press, U.K. 367 pp; Maccioni R. B. and Cambiazo V. (1995), Role of microtubule-associated proteins in the control of microtubule assembly, Physiol Rev. (4): 835-864). These present 3 or 4 segments of 18 amino acids each, highly preserved, which are separated by regions of about 13 amino acids (Maccioni R. B., Vera J. C., Dominguez J., Ávila J. (1989), A discrete repeated sequence defines a tubulin binding domain on microtubule-associated protein tau. Arch. Biochem. Biophys. 275 (2): 568-79). This binding domain (Maccioni R. B., Rivas C. I., Vera J. C. (1988), Differential interaction of synthetic peptides from the carboxyl-terminal regulatory domain of tubulin with microtubule-associated proteins, EMBO J. 7 (7):1957-63) is in charge of the assembling and stabilization of the microtubules (Mandelkow E. M., Biernat J., Drewes G., Gustke N., Trinczek B., Mandelkow E. (1995), Tau domains, phosphorylation, and interactions with microtubules, Neurobiol. Aging 16: 355-362). Besides, it has been demonstrated its association with other proteins such as G-actin.

Maccioni et al., 1989, schematized the general structure of the main isoform of the tau protein, h 67 (2N4R) having 441 amino acids.

Even though the tau protein is capable of undergoing a series of post-translation modifications (Pevalova M., Filipcik P., Novak M., Avila J., Iqbal K. (2006), Post-translational modifications of tau protein, Bratisl Lek Listy. 107 (9-10): 346-53), its phosphorylations plays a particularly important role in the regulation of its activity. The main tau isoform, presents 79 serines or threonines that act as potential phosphorylation sites (Lovestone S., Reynolds C. H. (1997), The phosphorylation of tau: a critical stage in neurodevelopment and neurodegenerative process, Neurosc. 78: 309-324). Accordingly, the combined activity of the different kinase proteins and phosphatase, that can act over the distinct forms of tau, can generate a high number of structural states in this proteins, containing different levels of phosphorylation in each one of these residues and in every isoform. Consequently, the equilibrium of these phosphorylation mechanisms verified by kinase proteins, and the dephosphorylation by phosphatase proteins, ultimately modulate a tau structural state that as a result defines its activity level (Mandelkow E. M., Biernat J., Drewes G., Gustke N., Trinczek B., Mandelkow E. (1995), Tau domains, phosphorylation, and interactions with microtubules, Neurobiol Aging 16: 355-362; Lovestone S., Reynolds C. H. (1997), The phosphorylation of tau: a critical stage in neurodevelopment and neurodegenerative process, Neurosc. 78: 309-324). Among the kinase proteins that phosphorylate tau at a cellular level is the calmodulin kinase, protein p38, and the Gsk3b enzymes (Rankin C. A., Sun Q. and Gamblin T. C. (2007), Tau phosphorilation by GSKβ promotes tangles-like filament morphology, Molecular Neurodegeneration 2:12) and cdk5 (also known as TPK II), the latter being involved in the control of the neurogenesis processes commanded by the tau activity (see Table 1) (Maccioni, R. B., Barbeito L., and Muñoz J. P. (2001), The molecular bases of Alzheimer's disease and other neurodegenerative disorders, Arch. Medical Research 32: 367-381; Reynolds C. H., Betts J. C., Blackstock W. P., Nebreda A. R., Andenson B. H. (2000), Phosphorylation sites on tau identifies by nanoelectrospay mass spectrometry, Differences in vitro between the Mitogen Activated Protein Kinase ERK2. c-Jun N Terminal Kinase and p-38, and Glycogen Synthase Kinase-3b, J. Neuroch. 74: 1587-1595).

It is interesting to notice that a protein like tau, crucial in the definition of neuron polarity and the processes of transport and growth cone generation in the axonal development, etc. (Kosik K. S., Orecchio L. D., Bakalis S., Neve R. L. (1989), Developmentally regulated expression of specific tau sequences, Neuron. 2 (4): 1389-97; Ferreira A., Cáceres A. (1991), Estrogen-enhanced neurite growth: evidence for a selective induction of Tau and stable microtubules, J. Neurosci. 11 (2): 392-400) requires being modulated by very precise mechanisms in order to accomplish its function in a controlled way. Consequently, important changes in this regulation can alter its capacity to bind to microtubules or to other elements of the cytoskeleton, or contribute to the generation of pathological conditions such as tau hyperphosphorylations, and the auto-aggregation that makes tau a protein with neurotoxic actions, such as the ones observed in an Alzheimer type degeneration (Sánchez M. P., Álvarez-Tallada V., Ávila J. (2001), La proteína tau en enfermedades neurodegenerativas, Taupatías, Revista de Neurología 33 (2): 169-177). As a difference with other proteins, the tau protein is resistant to temperature and acidic conditions, which in turn enables the process of separation of the MAPs and other thermolabile proteins such as tubulin. It is also possible to separate it from those that de-nature in presence of acids (Farias G. A., Munoz J. P., Garrido J., Maccioni R. B., Tubulin, actin, and tau protein interactions and the study of their macromolecular assemblies, (2002). J. Cell Biochem. 85: 315-324).

Garcia T., Jay D. phosphorylation of tau and Alzheimer disease, (2004), Gad. Med. Mex. 3: 329-33, specifically in table 1, shows tau phosphorylation sites, and the enzymes involved in this processes, from which it can be concluded that various kinases affect the tau phosphorylation in multiple places, the majority of which are found in the C-terminus end.

During the pathogenesis process of EA, tau begins to irreversibly hyperphosphorylate in multiple sites (García T., Jay D., Phosphorylation of tau and Alzheimer disease, (2004), Gad. Med. Mex. 3: 329-33, specifically table 1), and it integrates in anomalous filamentous structures called paired helical filaments (PHFs), to finally produce NFTs, losing in this way its physiological key functions such as the definition of the neuronal polarity and the control of axonal transport conveyed by microtubules (Maccioni R. B. and Cambiazo V. (1995), Role of microtubule-associated proteins in the control of microtubule assembly, Physiol Rev. 75 (4): 835-864). The tau hyperphosphorylation is the result of the imbalance of the action of different kinases and phosphatases, resulting in an hyperphosphorylated protein that has its normal function compromised causing as a consequence the neuronal damage (Buée L., Bassiére T., Buée-Scherrer V. (2000), Tau protein isoforms, phosphorylation and role in neurodegenerative disorders, Brain Res. 33: 95-130). Even though still under study it is accepted that at present the Aβ oligomers would be, among others, a triggering factor of the changes that lead to the alteration of the mechanism of neuronal signalisation (Roher A. E., Chaney M. O., Kuo Y. M., Webster S. D., Stine W. B., Haverkamp L. J., Woods A. S., Cotter R. J., Tuohy J. M., Krafft G. A., Bonnell B. S., Emmerling M. R. (1996), Morphology and toxicity of Abeta-(1-42) dimer derived from neuritic and vascular amyloid deposits of Alzheimer's disease, J. Biol. Chem. 271 (34): 20631-5; Lambert J. C., Pasquier F., Cottel D., Frigard B., Amouyel P., Chartier-Harlin M. C. (1998), A new polymorphism in the APOE promoter associated with risk of developing Alzheimer's disease, Hum. Mol. Genet. 7 (3): 533-40) and that lead to the tau hyperphosphorylation. Thus, this would be an early event in the progression towards the pathogenesis of AD. However the only established correlation between the intensity of the disorder and the pathologic lesions is presented with the neurofibrillary tangles (Maccioni, R. B., Barbeito L., and Muñoz J. P. (2001), The molecular bases of Alzheimer's disease and other neurodegenerative disorders, Arch. Medical Research. 32: 367-381).

The cytoskeleton of the eukaryotic cellules is the cellular structure responsible of the neuronal morphology. It is composed of microtubules, actin microfilaments and intermediate filaments (Maccioni R. B. and Cambiazo V. (1995), Role of microtubule-associated proteins in the control of microtubule assembly, Physiol Rev. 75 (4): 835-864; Ávila J., Lucas J. J., Pérez M. and Hernández F. (2004), Role of Tau Protein Both Physiological and Pathological Conditions, Rev. Physiol. 84: 361-384). These polymers coexist in an interweaved form by means of a type of dynamic macromolecular interaction that define the organisation of this network, which extends in the wide domain of the cytoplasm and interacts even with the cellular membrane, the nucleus and cellular organelles such as centrosomes, mitochondrie, lysosomes, etc. (Maccioni R. B. and Arechaga J. (1987), "The Cytoskeleton in Cell Differentiation and Development", Oxford University Press, U.K. 367 pp; Maccioni R. B. and Cambiazo V. (1995), Role of microtubule-associated proteins in the control of microtubule assembly, Physiol Rev. 75 (4): 835-864).

The microtubules are essential cytoskeleton components, responsible of the formation and maintenance of the axons, dendrites and specific contacts. The MAPs proteins contribute to the dynamism and stability of the microtubules. Among them there are the MAP1A, MAP1B, MAP2 proteins and finally the tau protein (Maccioni R. B. and Cambiazo V. (1995), Role of microtubule-associated proteins in the control of microtubule assembly, Physiol Rev. 75 (4): 835-864; Ávila J., Lucas J. J., Pérez M. and Hernández F. (2004), Role of Tau Protein Both Physiological and Pathological Conditions, Rev. Physiol. 84: 361-384)

The tau protein is important in the maintenance of the neuronal polarity and in the stabilization of a defined architecture in the differentiated neuron. Besides, it has been demonstrated that the tau activity is key to the morphogenesis of the growing cones in the cerebral neurons, in which structure also participate the local actin filament networks (Paglini G., Pigino G., Kunda P., Morfini G., Maccioni R., Quiroga S., Ferreira A., Cáceres A. (1998), Evidence for the participation of the neuron-specific CDK5 activator P35 during laminin-enhanced axonal growth, J. Neurosci. 18 (23): 9858-9869). Furthermore, a main role in the promotion of the axon growth is suggested (Black M. M., Slaughter T., Moshiach S., Obrocka M. and Fischer I. (1996), Tau is enriched on dynamic microtubules in the distal region of growing axons, J. Neuroscience. 16: 3601-3619). On the other hand, MAP-2 would rather be related to the generation of short processes in the neuron.

Quinolines are organic heterocyclic aromatic compounds, having linked benzene rings, wherein the $C_1$ is constituted of a Nitrogene atom. The quinolines have applications both at industrial and clinical level. It can be noted that mainly at a clinical level some quinoline derivatives have been found to be active as anaesthesic, anti-tumor and anti-malaria drugs (Campbell S. F., Hardstone J. D., Palmer M. J. (1988). 2,4-Diamino-6,7-dimethoxyquinoline derivatives as alpha 1-adrenoceptor antagonists and antihypertensive agents, J. Med. Chem. 31 (5): 1031-5).

Specially, the quinolines used as anti-malaria owe their origin to quinine, substance used as an antipyretic for hundreds of years. Nevertheless, quinine has some drawbacks associated to its toxicity and its administration, so related substances have been synthesized, such as chloroquine, that is a quinoline developed during World War II and that is nowadays the principal weapon used against human paludism (Ridley R. (2002), Medical need, scientific opportunity and the drive for anti-malarial drugs, Nature 415: 686-93). According to its effectiviness against the different stages by which the vital cycle of plasmodium evolves, the quinoline-type antimalarial agents have been classified as "erythrocytic schizogony-cides", that act in the asexual erythrocytic stages of the parasites, interrupting the erythrocytic schizogony, stopping in this manner the infection and finally eliminating the parasites from the body (Baird J. K., Basri H., Subianto B., Fryauff D. J., McElroy P. D., Leksana B., Richie T. L., Masbar S., Wignall F. S., Hoffman S. L. (1995), Treatment of chloroquine resistant Plasmodium vivax with chloroquine and primaquine of halofantrine, J. Infect. Dis. 171: 1678-82). Due to these uses of quinolines, studies of pre-clinic and clinic phase have been accepted, and so their use in human beings has been approved.

In particular, U.S. Pat. No. 7,117,830 and publication US N° 2005//009865 describe the use of certain quinoline derivatives in the diagnosis of diseases related with the accumulation of the tau protein. Particularly, these documents disclose the compounds: a) 4-[2-(2-benzimidazolyl)ethenyl]-N,N-diethylbenzenamine (BF-126), 2-[(4-methylamino)phenyl]quinoline (BF-158) and 2-(4-aminophenyl)quinoline (BF-170), and other quinoline phenyl derivate compounds, that are used for in-vivo magneto-imaging for the tau pathology in Alzheimer's disease. Besides, they demonstrate the low affinity for beta-amyloid fibres and the high affinity for tau neurofibrillary tangles, as well as other characteristic effects of the Alzheimer's disease.

Publication WO 2008/049047 discloses quinoline derivatives useful in the treatment of diseases related with the liver X receptor, such as the acute coronary syndrome, Alzheimer, diabetes and atherosclerosis. However, the R1 radical of said document always consists of an alkyl derivative, while in the present invention the corresponding R2 radical is a phenyl radical.

EP 1574500 (A1) discloses structurally different quinoline derivatives to the quinoline derivatives of the present invention, which can also be used for diagnosis images of diseases in which the tau protein is accumulated, and compositions and kits thereof. Furthermore, it discloses a method to stain neurofibrillary tangles in brain samples, and a pharmaceutical composition for the treatment and/or prophylaxis of a disease wherein the beta sheet structure is the cause or possible cause of the disease.

WO 2009/097401 and WO 2009/097278 disclose compounds derived from 2-amine-quinoline and from 6-substituted-thio-2-amine-quinoline, structurally different from the quinoline compounds of the present invention, that inhibit β-secretase, known as the β site amyloid cleavage enzyme, BACE, BACE 1, Asp2 or mempasin2, pharmaceutical compositions that have them and their use in the treatment of the Alzheimer's disease, senility, dementia and mild cognitive impairment.

WO 2009/133692 discloses quinoline derived compounds, structurally different from the quinoline compounds of the present invention, useful in the treatment and/or prophylaxis or arteriosclerosis such as atherosclerosis and arteriosclerosis associated with diabetes, dyslipidemia, hypercholesterolemia, diseases related with lipids, inflammatory diseases induced by an inflammatory cytokine, skin diseases such as allergic skin diseases, diabetes or Alzheimer's disease, senility, dementia and mild cognitive impairment.

Consequently, after failed attempts with drugs that disassemble the senile amyloid plaques, a big part of the efforts at world level are being directed to smaller tau aggregates and to the same neurofibrillary tangles (NFTs), whereas the present inventions provides quinoline compounds that inhibit the formation and at the same time disaggregate the NFTs, and in consequence would be useful in the treatment and prophylaxis of the Alzheimer's disease.

DESCRIPTION OF THE INVENTION

Figure 1:
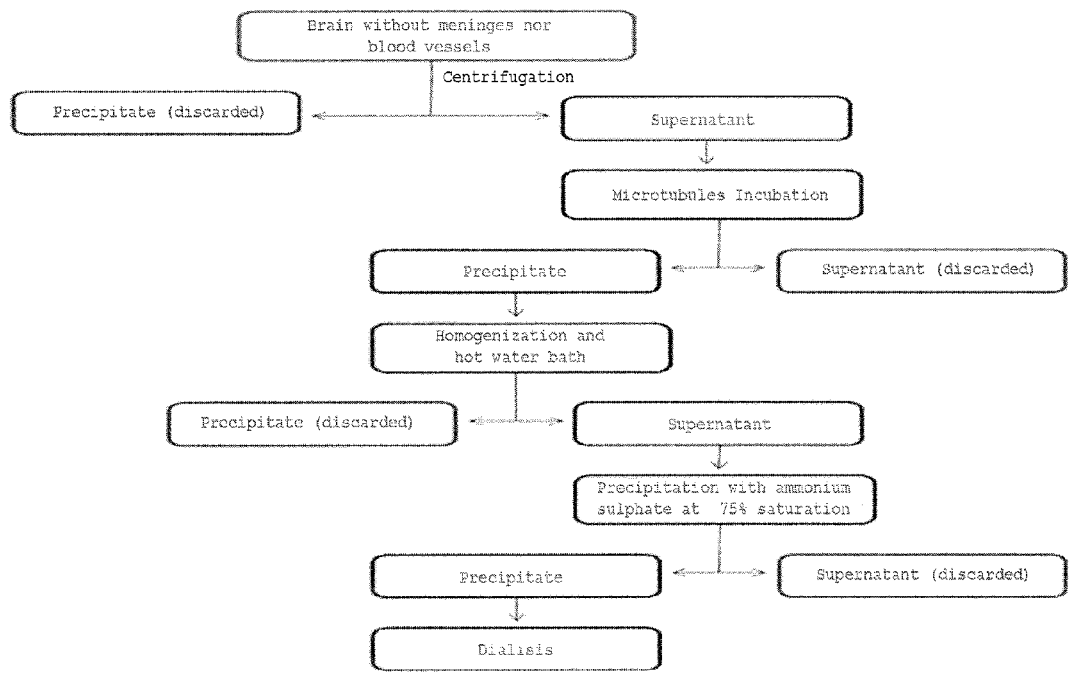
FIG. 1 shows the tau purification procedure developed in the invention. In particular it summarizes the main steps of the purification.

According to the data presented hereinbefore and under the context that the NFTs deposits in the neurons can lead to a gradual neurodegenerative process, and on the basis that these quinolines have certain affinity for tau protein (Okamura N., Suemoto T., Furumoto S., Suzuki M., Shimadzu H., Akatsu H., Yamamoto T., Fujiwara H., Nemoto M., Maruyama M., Arai H., Yanai K., Sawada T., Kudo Y. (2005), Quinoline and bencimidazole derivatives: candidate probes for in vivo imaging of tau pathology in Alzheimer's disease, J. Neurosci. 25: 10857-10862), the inventor conducted a search for molecule ligands that bind the tau protein, and especially to the Alzheimer polymerized-type tau, as potential blockers of the aggregation of hyperphosphorylated tau before the formation of the NFTs, evaluating the capability of a family of quinolines of clinical relevance and their derivatives (THQs) (see Table 1 hereinafter) to inhibit the aggregation of the tau protein in the form of PHFs produced in vitro, in a possible therapeutic route for AD.

TABLE 1

Quinoline derivatives used for the evaluation in the disaggregating of tau protein:

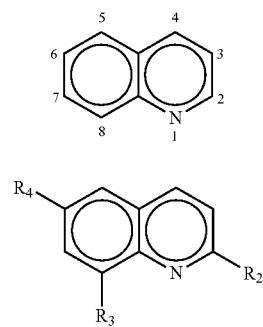

| Compound | R$_2$ | R$_4$ | R$_3$ |
|---|---|---|---|
| 1) THQ 3-S | 4-methylphenyl | —OMe | —H |
| 2) THQ 4-S | 4-methylphenyl | —Me | —H |
| 3) THQ 55 | 4-aminophenyl | —Me | —H |
| 4) THQ 56 | 4-aminophenyl | —H | —H |
| 5) THQ 9-S | 4-methylphenyl | —H | —Br |
| 6) THQ 12-S | 5-methylphenyl | —Me | —H |

1) 2-(4-methylphenyl), 6-(O-methyl)quinoline (THQ-3S)
2) 2-(4methylphenyl), 6-(methyl)quinoline (THQ-4S);
3) 2-(4-aminophenyl), 6-(methyl)quinoline (THQ-55)
4) 2-(9-aminophenyl)quinoline (THQ-56);
5) 2-(4-methylphenyl), 8-(bromo)quinoline (THQ-9S); and
6) 2-(5-methylphenyl), 6-(methyl)quinoline (THQ-12S)

The already mentioned linking molecules that interact with the brain tau protein and can affect the auto-generation processes of this hyperphosphorylated protein in pathological conditions were evaluated, having as an objective the biomedical applications in the investigation of the Alzheimer's disease domain.

To carry out this objective the following process was followed:

brain tau protein and the paired helical filaments (PHFs) from human brains and bovine tau protein were isolated and characterized, all of which were induced to polymerize with heparin (Mandelkow E. M., Mandelkow E. (1993), Tau as a marker for Alzheimer's disease, Trends Biochem Sci. 18 (12): 480-3);

the octanol/water partition coefficient was established and experimentally correlated the liposolubility with the capacity of quinolines to cross the hemato-encephalic barrier (BHE);

tau protein helical filaments were produced and characterized starting from the isolated and recombinant proteins. Alternatively, starting from the Aβ1-42 recombinant peptide, amyloid aggregates were produced and characterized;

the interaction of the selected quinolines with tau protein and its aggregated forms was studied and characterized; and theoretic docking computing studies are carried out to establish possible interaction sites of the assayed compound in the protein structure.

For the development of the indicated relations, bovine brains recently slaughtered and/or post-mortem human brains stored at −80° C. that belonged to Alzheimer patients were used.

Human PHFs were obtained, which were purified from human brains using affinity columns.

The quinolines of biomedic importance within the context of this invention, directed to the Alzheimer's disease treatment, as described before in Table 1, were obtained by organic synthesis.

The samples of quinolines were prepared at a concentration of 1.0 mg/mL in methanol and serial dilutions were carried out at different concentrations, for which their fluorescence was established with an excitation wave length at 290 nm and an emission of between 260 and 500 nm.

The partition coefficient (log $P_{o/W}$) was established as described in Takacs-Novak K., Nagy P., Jozan M., Orfi L., Dunn W. J. 3rd, Szasz G. (1992), Relationship between partitioning properties and (calculated) molecular surface, SPR investigation of midazoquinazoloneb derivatives, Acta. Pharm. Hung. 62 (1-2): 55-64, wherein 2 phases are used, an aqueous phase comprising a buffer solution PBS 0.1× pH 7.4 that is saturated with an n-octanol solution that comprises the organic phase.

Stock solutions at 1.0 mg/mL of each quinoline being studied were prepared in PBS buffer 0.1× pH 7.4 saturated in octanol. Quinolines samples THQ 9S and THQ 12S (see Table 1) were treated by zonication for no longer than 30 seconds, due to their viscous nature. Starting from these solutions, dilutions were made for a range concentration of between 1.0 mg/mL and 100 μg/mL to establish their maximum absorbance in the UV-visible region.

Then the tested quinolines were dissolved in PBS 0.1× pH 7.4 saturated in n-octanol and agitated for 30 min. at room temperature. Subsequently, this emulsion was left to settle for 48 h and a centrifugation at 3,000 rpm for 10 minutes was carried out to separate the phases. Both the octanol/water partition coefficient and Log P were established using the difference in the absorbance in the UV-visible region for each compound using equation 1:

$$[THQ \text{ in octanol}] = [THQ \text{ start}] - [THQ \text{ buffer}] \quad \text{Eq. 1}$$

Wherein:

[THQ buffer]=concentration established by the absorbance of each sample

The concentrations for THQ start are established using equation 2:

$$[THQ \text{ start}] = \frac{100 \, \mu L \times [THQ \text{ concentration in methanol}]}{10,000 \, \mu L} \quad \text{Eq. 2}$$

Subsequently, the P quotient in established between both phases as described by equation 3:

$$P = \frac{[THQ \text{ in octanol}]}{[THQ \text{ buffer}]} \quad \text{Eq. 3}$$

Finally the partition coefficient is established by Log P.

For this test 2 controls were used: clidinium bromide that is a quaternary amine that is not liposoluble, and sodium thiopental, which is a very liposoluble barbituric anaesthetic. Each part of the test was done in triplicate.

The tau protein is obtained essentially according to the Farías method (Farías G. A., Vial C., and Maccioni R. B. (1992), Specific macromolecular interactions between tau and the microtubule system, Molecula and Cellular Biochemistry, 112: 81-88) with minor modifications. Bovine brains recently slaughtered and/or post-mortem human brains stored at −80° C., are cleaned from meninges, blood vessels and superficial blood, and are processed according to the repetitive assembly and disassembly cycles protocol, dependant on temperature.

Brain regions like the temporal and frontal lobe, that are affected by AD, are homogenized at 4° C. in homogenization buffer (solution A). The homogenate is centrifuged at 42,000 g (19,450 rpm using a T647.5 rotor) for 30 min. at 4° C.; stage at which the supernatant is collected. Then to this supernatant the necessary MT polymerization components (solution B) are added. This solution is incubated for 1 h at 37° C. with gentle agitation. The more viscous liquid obtained is divided into the tubes of the centrifuge. Subsequently, the microtubules formed are rescued from the pellet formed by centrifugation at 42,000 g for 30 min at 37° C. This microtubules pellet is then treated with the microtubules homogenization buffer (solution C). The volume to prepare is approximately 60 mL (3 volumes of solution per each volume of pellet).

Subsequently, homogenization takes place on ice using a dounce homogenizer for 15 min. This step is key in the tau yield. The obtained slurry undergoes a hot water bath at 100° C. for 5 min. in order to precipitate tubulin and other contaminants that are thermolabile. Afterwards, this slurry is centrifuged at 42,000 g for 30 min. at 4° C., stage at which the supernatant is saved and treated with ammonium sulphate at a 75% saturation overnight at 4° C. in order to precipitate the tau protein (Farias G. A., Munoz J. P., Garrido J., Maccioni R. B., Tubulin, actin, and tau protein interactions and the study of their macromolecular assemblies, (2002) J. Cell. Biochem. 85: 315-324). Subsequently, it is centrifuged at 42,000 g for 30 min. at 4° C. wherein the precipitate is re-suspended in solution D and dialyzed to eliminate salts. The dialysis is carried out in dialysis membranes of a known pore (12 kDa size) at 4° C. and under agitation for 24 h with three changes of Tris-HCl 2.5 mM buffer during the 24 h. The resulting solution is concentrated using a "Centricon ultrafiltration" system in a centrifugation at 2,000 g for 30 min. at 4° C. FIG. 1 summarizes the steps carried out for tau purification.

The protein concentration is established using the Bradford method (Bradford M. M. (1976), A Rapid and Sensitive Method for the Quantitation of Microgram Quantities of Protein Utilizing the Principle of Protein Dye Binding, Analytical Biochem. 72: 248-254) using bovine albumin serum for the calibration plotting.

After purification of the tau protein and the establishment of its concentration, even quantities of protein were loaded onto polyacrylamide denaturing gels at 10% (Laemmli U.K. (1970), Cleavage of structural proteins during the assembly of the head of bacteriophage T4, Nature 227 (5259): 680-5); then they were transferred to a nitrocellulose membrane and this one was blocked with skimmed milk at 5% in PBS buffer. Subsequently, the membranes are incubated overnight at 4° C. with a primary antibody (dilution 1:1000 in skimmed milk at 1% in PBS 1×). After three washes with PBS-Tween (0.05%) the membranes were incubated with a secondary antibody (dilution 1:1000 in skimmed milk at 1% in PBS 1×) associated to peroxidase. Finally, the detection was carried out using a luminescent system and the samples were analyzed on photographic plates.

The following primary antibodies were used for the immunodetection: to study the states of tau protein phosphorylation the AT8 antibody was used, that recognizes the $Ser^{202}$ and $Thr^{205}$ phosphorylated epitopes in tau protein,; Tau 5 that recognizes tau protein epitopes, independently of their phosphorylation state; and RBX anti β-amyloid 1-42, that recognizes the β-amyloid peptide of 42 amino acids in length. All of these antibodies were used according to the producer's instructions.

Protein Aggregation Studies

Effect of quinolines in tau aggregation. Electronic microscopy studies (ME). The purified and highly concentrated tau protein is induced to polymerization in the form of PHFs in the presence of polyanions (heparin at a concentration of 200 μg/mL) in a final volume of 10 μL. This mixture is incubated at 37° C. and maintained under gentle agitation for 7 days. At the same time, another sample containing the tau protein, heparin (200 μg/mL) and the different quinolines in the study (THQ 4S and THQ 55 (see Table 1)) were incubated in the same way at a concentration of 10 μM and final volume of 10 μL, verifying by these means the effect that quinolines have in the polymerization of this protein. In parallel, a study was conducted using recombinant tau protein at a concentration of 2.0 mg/mL prepared in distilled water. Table 2, summarizes the parameters of this experiment.

The aggregates thus formed were visualized using electronic microscopy with negative stain using 2% uranyl acetate. Finally, the number of fibers per visual field were counted, and the length and width of the same were measured, observing an average of 25 visual fields.

TABLE 2

Tau protein aggregation studies.

|  | +Control | −Control | Sample under study |
|---|---|---|---|
| Tau protein 2.0 mg/mL | X | X | X |
| Heparin 200 ug/mL | X | — | X |
| Bi distillated water | — | X | — |
| Quinoline 10 uM | — | — | X |

As positive control, a tau and heparin-containing solution (without quinoline) was used, and as negative control, tau and water, while the samples under study had tau, heparin and the quinolines THQ 4S or THQ 55 (see Table 1) at concentrations of 10 μM.
The "X" indicates presence and the "—" indicates absence.

Effect of the quinolines in the PHFs disassembly. ME studies. The PHFs, at a concentration of 400 μg/mL, are incubated with the quinolines under study at a final concentration of 10 μM in a volume of 10 μL at 37° C. under gentle agitation for 7 days. The results were visualized with electronic microscopy, using negative stain with 2% uranyl acetate.

Effect of the quinolines in the Aβ 1-42 peptide aggregation. ME studies. The Aβ 1-42 peptide was dissolved in PBS 1× pH 7,4 buffer, sterilized and filtered, obtaining a solution of a final concentration of 1.0 mg/mL in a final volume of 100 μL. In order to have a comparison parameter with tau protein, the Aβ 1-42 peptide was induced to polymerization in the form of Aβ fibrils and aggregates. This solution was incubated at 37° C. and maintained at gentle agitation for 7 days (Ward R. V., Jennings K. H., Jepras R., Neville W., Owen D. E., Hawkins J., Christie G., Davis J. B., George A., Karran E. H., and Howlett D. R. (2000), Fractionation and characterization of oligomeric, protofibrillar and fibrillar forms of beta-amyloid peptide, Biochem. J. 348: 137-144). At the same time, and in the same way, another sample containing the Aβ 1-42 peptide and the different quinolines under study (THQ 4S and THQ 55 (see Table 1)), were incubated in the same way at a concentration of 10 μM in a final volume of 100 μL, thus verifying the effect that the quinolines have over the Aβ 1-42 peptide aggregation. Table 3 summarizes the parameters of this experiment.

The so formed aggregates were visualized with electronic microscopy, using negative stain with 2% uranyl acetate. Finally, the number of fibers per visual field were counted, and the length and width of the same measured, observing an average of 25 visual fields.

TABLE 3

Aβ 1-42 peptide aggregation studies.

|  | +Control | −Control | Sample under study |
|---|---|---|---|
| Aβ 1-42 peptide | X | X | X |
| Quinoline | — | — | X |

As a positive control a solution containing the β-amyloid peptide at a concentration of 1.0 mg.mL under agitation at 37° C. was used, in contrast with the negative control that also contains the β-amyloid peptide but that is stored at −80° C. and thus not polymerizing, while the samples under study contained the β-amyloid peptide and the THQ 4S and THQ 55 quinolines (see Table 1) at concentrations of 10 μM.
The "X" indicates presence and the "—" indicates absence.

Preparation of the samples for electronic microscopy. The tau, Aβ 1-42 and PHFs protein aggregates were visualized with electronic microscopy, using negative stain with uranyl acetate. To achieve this, 6.0 μL of the sample was used (tau, PHFs or Aβ 1-42 aggregates), placed in a copper grid (pre-treated with parlodion and carbon vapour) and adsorbed for 1 minute at room temperature. The excess sample was removed with filtration paper. Subsequently, 6.0 μL of 2% uranyl acetate prepared with bi-distilled water was disposed over the grid, left to dry for 30 seconds and used for the negative stain. Finally, the grids were examined under the microscope.

Effect of the quinolines in the tau aggregation. Turbidimetric studies. Tau aggregation was monitored by means of its absorbance at λ 340 nm using UV spectrophotometry. Purified and highly concentrated tau protein from bovine brain (2.0 mg/mL) was re-suspended in MES 0.1 M pH 7.2 buffer and induced to polymerize in the form of PHFs in the presence of polyanions (heparin at a concentration of 200 μg/mL) at a final volume of 1.0 mL. This mixture was incubated at 37° C. and maintained under gentle agitation for 7 days. At the same time, another sample containing the tau protein, heparin (200 μg/mL) and the selected quinoline at different concentrations from 1.0 to 50 μM and a final volume of 1.0 mL was incubated in the same way, thus verifying the effect that quinolines have over tau aggregation. Table 4 summarizes the parameters of this experiment. It is known that some benzimidazole derivatives do not prevent tau aggregation; under this context a control was used that contained tau (2.0 mg/mL), heparin (200 μg/mL) and Astemizol at a concentration of 10 μM. As an additional control the tau protein was replaced with water in order to measure the absorbance of these quinolines. Each sample was carried out in triplicate.

TABLE 4

Turbidimetric study of tau aggregation in presence and absence of quinolines.

|  | Control + | Control − | Tau + THQ 55* 1.0 mM | Tau + THQ 55* 10 mM | Tau + THQ 55* 50 mM | Tau + AST 10 mM |
|---|---|---|---|---|---|---|
| tau protein (2.0 mg/mL) | X | X | x | x | x | x |

TABLE 4-continued

Turbidimetric study of tau aggregation in presence and absence of quinolines.

| | Control + | Control − | Tau + THQ 55* 1.0 mM | Tau + THQ 55* 10 mM | Tau + THQ 55* 50 mM | Tau + AST 10 mM |
|---|---|---|---|---|---|---|
| Heparin (200 µg/mL) | X | — | x | x | x | x |
| MES (0.1M) | X | X | x | x | x | x |
| THQ 55* | — | — | x | x | x | — |
| AST | — | — | — | — | — | x |
| Distilled water | — | X | — | — | — | — |

As positive control a solution containing tau, and heparin was used, and as negative control tau and water, while the samples under study contained tau, heparin and THQ 55 quinoline (see Table 1) at different concentrations between 1.0 and 50 µM. The other aggregation control contained tau, heparin and Astemizol (AST) at a concentration of 10 µM.
The "X" indicates presence and the "—" indicates absence.
*see Table 1

Effect of quinolines in tau aggregation. Sedimentation studies. After 7 days of incubation at 37° C. under gentle agitation, the sedimentation of the tau aggregates was conducted in the presence and in absence of quinolines. To this purpose, 400 µl were taken of each one of the samples prepared for the turbidimetric analysis and they were centrifuged at 42,000 g (18.000 rpm using the AH-650 rotor) at 37° C. for 25 min. The pellet obtained from each sample of this centrifugation was re-suspended in 50 µL of MES 0,1 M slightly alkaline (pH 7,2) buffer and the concentration of protein was established for each one of them. In this procedure, and because the sample volume is very small, a nanophotometer was used, measuring the concentration of the sedimented and re-suspended protein at λ 280 nm.

Figure 2:
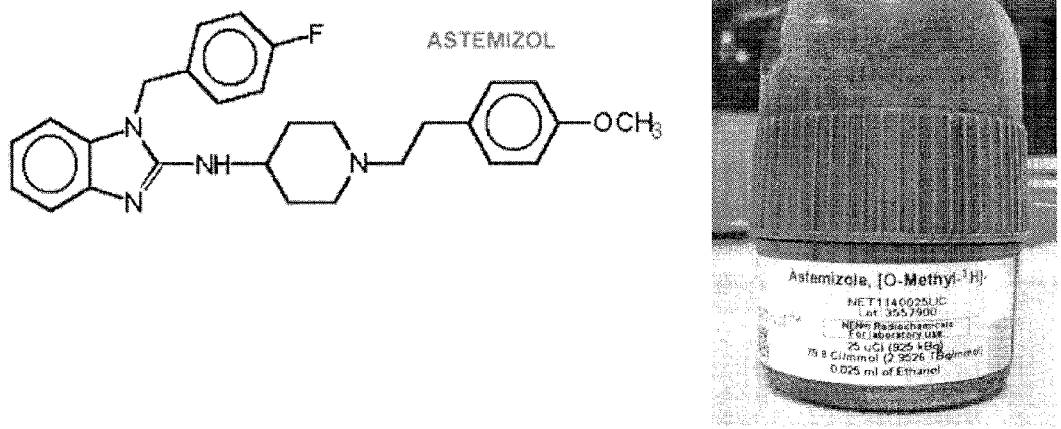
FIG. 2 shows the structure of astemizole, benzimidazole used in the binding and displacement tests and its radioactive isotope $^3$H-AST, for the evaluation of the interaction of the quinolines with the tau protein system.

Interactions of quinolines with tau and in vitro displacement tests with $H^3$-AST. In previous laboratory tests by the inventor and also from other authors (Okamura N., Suemoto T., Furumoto S., Suzuki M., Shimadzu H., Akatsu H., Yamamoto T., Fujiwara H., Nemoto M., Maruyama M., Arai H., Yanai K., Sawada T., Kudo Y. (2005), Quinoline and becimidazole derivatives: candidate probes for in vivo imaging of tau pathology in Alzheimer's disease, J. Neurosci. 25: 10857-10862; Rojo L., Avila M., Chandia M., and Maccioni R. B. (2007), $^{18}$F Lansoprazole as PET radiotracer, Chemical and biological studies towards the development of a New PET Radiotracer, International Conference on Clinical PET and Molecular Nuclear Medicine. 10-14 November, Bangkok) the Kd and binding maximums specific to some benzimidazols of clinical use were established, among them [O-methyl-3H]-astemizol (FIG. 2) through the interaction established with the tau protein. With this background Scatchard and displacement tests are performed with the quinolines mentioned before.

Figure 3:
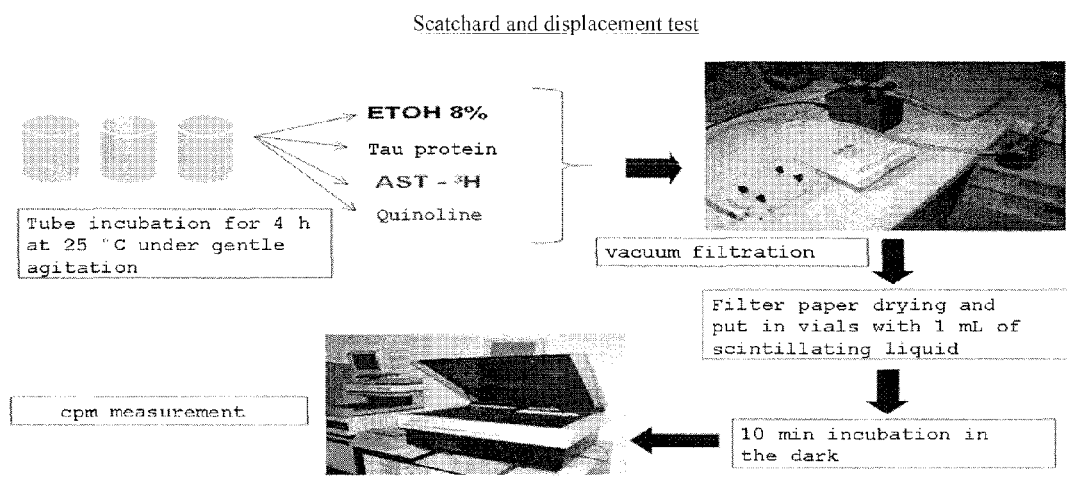
FIG. 3 is a schematic illustration of the procedure used for the Scatchard and $^3$H-AST displacement tests with quinolines in vitro.

The diagram of FIG. 3 summarizes the procedure used in both experiments.

For the Scatchard test a fixed tau protein concentration (230 nM) and variable concentrations of $^3$H-AST between 10 and 120 nM was used, leading to a final volume of 20 µL with 8% ethanol (EtOH 8%). The tau protein underwent treatment previous to this test, incubating the same at 37° C. under gentle agitation for 7 days. Subsequently the tau protein and $^3$H-AST were incubated for 4 h at 25° C. under gentle agitation. Then this solution was filtered under vacuum for 10 minutes and the filtering papers were dried at room temperature, and transferred to a vial with 1.0 mL of scintillating liquid. It is then left in the dark and finally the counts per minute (cpm) are measured in a scintillating counting equipment.

In the test of displacement of the drug, the same procedure indicated before is used, with the only difference being a fixed hTau protein and $^3$H-AST concentration (230 nM and 52 nM respectively), and variable concentrations of the cold ligand (THQ 4S and THQ 55 (see Table 1, separately)) between 10 nM and 10 µM (as indicated in Table 6) leading to a final volume of 20 µL EtOH 8%. Subsequently, the tau protein, $^3$H-AST and the quinolines are incubated for 4 hours at 25° C. under gentle agitation and the procedure depicted in FIG. 3 is followed.

TABLE 5

THQ 4S and THQ55 quinolines concentrations used in the displacement tests.

| Quinoline concentration (nM) | 0 | 10 | 25 | 50 | 100 | 200 | 500 | 1.000 | 5.000 | 10.000 |
|---|---|---|---|---|---|---|---|---|---|---|

The cold ligand (THQ 4S and THQ55 (see Table 1, separately)) was used in variable concentrations between 10 nM and 10 µM. $^3$H-AST and tau protein were used in fixed concentrations of 52 nM and 230 nM, respectively.

Docking tests. For the computerized studies it was necessary to obtain the crystallized structure of a tau protein fragment. The structure of a penta-peptide consisting in a structural nucleus of the PHFs located in the C-terminus was obtained from the "Protein Data Bank" (PDB) public data base. 2V17:A, is the PDB code of $^{387}$DHGAE$^{391}$. With this small fragment the Docking studies were carried out in order to obtain an approximation of the logarithms that make possible to predict the interaction that happens between the quinolines and the tau protein.

Statistical analysis: The calculations of the standard deviation were carried out in the Excel spreadsheet (Microsoft Office XP), which performs a measurement of dispersion of the values in relation to the mean (average value).

Observations: DESVEST is based on the hypothesis that the arguments represent the sample of a population. If its data represent the total population, DESVESTP is used to calculate the standard deviation.

The standard deviation is calculated the usinf the unbiased or "n−1" method.

DESVEST uses the following formula:

$$\sqrt{\frac{n\sum x^2 - (\sum x)^2}{n(n-1)}}$$

$$\sqrt{\frac{n\sum x^2 - (\sum x)^2}{n(n-1)}}$$

The texts and logical values such as TRUE or FALSE are not taken into account.

Fluorescence Tests.

This test was carried out to establish the interaction between the quinolines and the tau protein and to obtain a fluorescence pattern of both molecules (Friedhoff P., Schneider A., Mandelkow E. M., and Mandelkow E. (1998), Rapid Assembly of Alzheimer-like Paired Helical Filaments from Microtubule-Associated Protein Tau Monitored by Fluorescence in Solution, Biochemistry 37: 10223-10230), discovering that these compounds generate a low fluorescence and in a high concentration (higher than 1.0 mg/mL), which implies using a higher quantity of protein, at the time of performing the binding tests and the establishment of Kd, Ki and Bmax constants, which is a limiting aspect due to the levels of production.

In this way it was found that the THQ 55 quinoline (see Table 1) was the compound that showed best results. This quinoline was at a concentration of 1.0 mg/mL and it was excited at λ 290 nm, presenting an emission at λ 350 and 480 nm. The fluorescence intensity was of 80 and 30 from a maximum of 1000 in the first test, and 30 and 478 from a maximum of 1000, in this latter case increasing the "slip" or light opening in the equipment. Fluorescence assays were also performed for THQ 4S and THS 12S quinolines (see Table 1) but the fluorescence intensity was too low (lower than 10 with a maximum of 1000) even when increasing the opening of the slip.

Figure 4A:
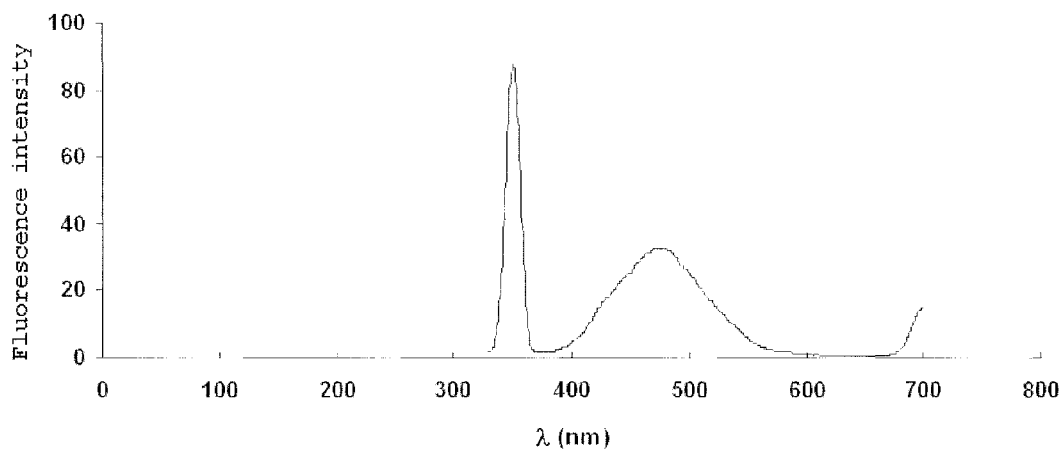
FIG. 4a shows the fluorescence pattern for THQ 55 (see Table 1 hereinafter) excited at 290 nm and emission at 380 an 480 nm with a 2.0 slit.
Figure 4B:
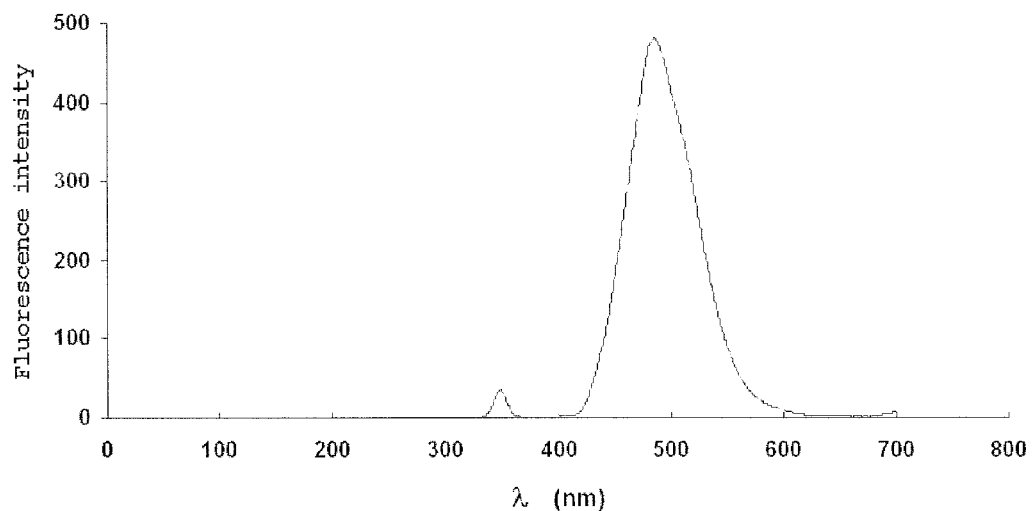
FIG. 4b shows the fluorescence pattern for THQ 55 (see Table 1 hereinafter) excited at 290 nm and emission at 380 and 480 nm, with a 5.0 slit.

FIGS. 4a) and 4b) show the results obtained in the establishment of the fluorescence for THQ 55 (see Table 1).

Determination of the Octanol/Water Log P Partition Coefficient.

Figure 5:
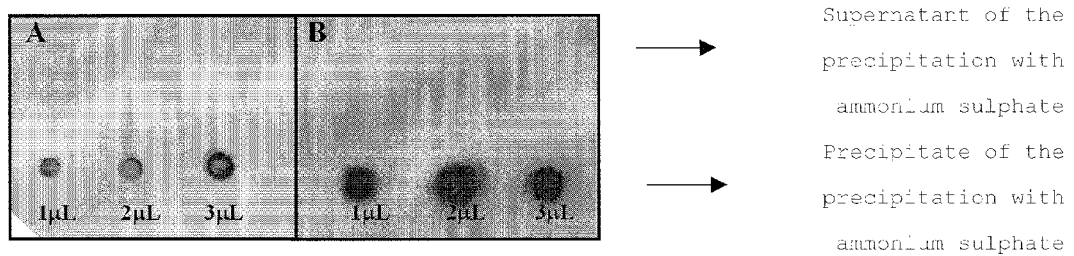
FIG. 5 shows the tau dotblots of a bovine brain. Pureness characterization of the tau protein. The upper part of the figure illustrates the supernatant obtained from the precipitation with ammonium sulphate and the lower part to the precipitate from the precipitation with ammonium sulphate. A) dotblot for hTau. B) dotblot for bTau.

According to the working hypothesis, what we search in these molecules is to evaluate if they can reach the brain and exert their effect in the affected zones in persons that suffer AD. In this context, the first step is the determination of the liposolubility expressed as Log P. The physico-chemical and pharmacokinetic characteristics of this drugs (Table 6) indicate that its liposolubility (expressed as Log P) is relatively high.

sis. For the dotblots, Tau-5 was used as a primary antibody and mouse antiIgG developed in goat conjugated with peroxidise as secondary antibody (FIG. 5).

Figure 6:
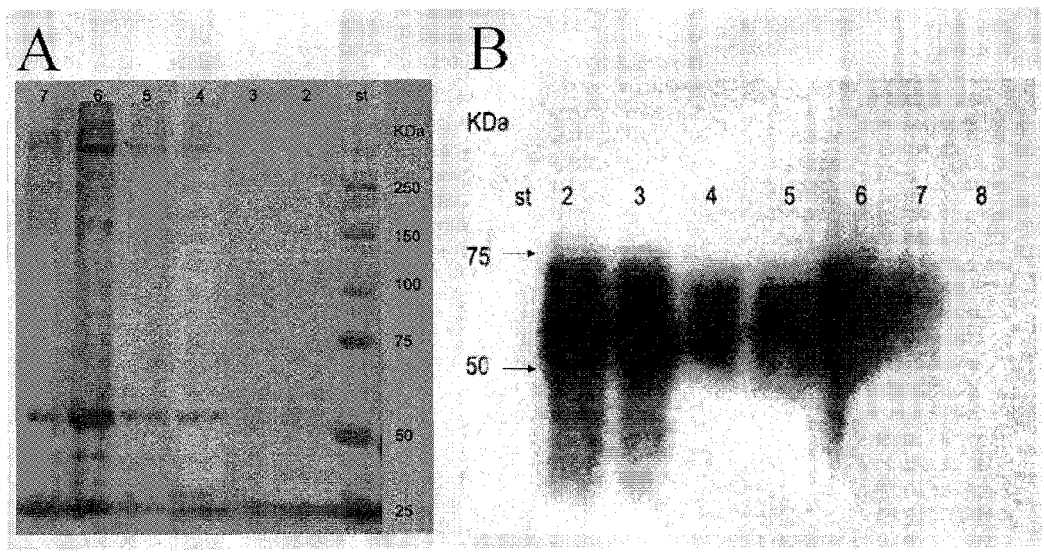
FIG. 6 shows the tau protein purification procedure. A) SDS-PAGE. Shows the characterization of bovine tau protein (bTau) obtained from the purification with ammonium sulphate. Lane 1: Molecular weight standard All Blue (catalog #161-0373 BIO-RAD); Lanes 2 and 3: 6.0 µL of supernatant from the precipitation with ammonium sulphate; Lanes 4 and 5: 6.0 µL bovine tau (bTau) 3.36 mg/mL (used as a positive control); Lanes 6 and 7: 6.0 µL bTau 10.0 mg/mL. B) Western blot: Shows the different tau isoforms obtained in the purification of this protein. The presence of the protein isoforms is established, and are found to be between 55 kDa and 65 kDa, both for the bTau purification (lanes 2 and 3) and for the hTau (lanes 6 and 7). Lane 1: Molecular weight standard All Blue (catalog #161-0373 BIO-RAD); Lanes 2 and 3: 6.0 µL of bovine tau (bTau) 10.0 mg/mL; Lanes 4 and 5: 6.0 µL bovine tau (bTau) 3.36 mg/mL; Lane 6: 6.0 µL hTau 1.3 mg/mL; Lane 7: 6.0 µL hTau 0.65 mg/mL.

Using this technique, it was established that all of the tau protein is obtained in the precipitate with ammonium sulphate salts and not in the supernatant. Using SDS-PAGE and Western Blots, the patterns of the tau isoforms that are present in the precipitate obtained from the purification were established (FIG. 6).

Using the MicroBradford technique the concentrations of both bTau and hTau obtained in the purification were determinated. Subsequently a lyophilization was carried out so as to concentrate each one of the samples of both hTau and bTau, of which adequate concentrations for the subsequent studies were obtained, with a 12% to a 14% of yield for tau purification, all of which is in accordance to the method described by Farías G. A., Vial C., and Maccioni R. B. (1992), Specific macromolecular interactions between tau and the microtubule system, Molecula and Cellular Biochemistry, 112: 81-88; Farias G. A., Munoz J. P., Garrido J., Maccioni R. B., Tubulin, actin, and tau protein interactions and the study of their macromolecular assemblies, (2002) J. Cell Biochem. 85: 315-324). Table 7 indicates the total quantity of protein obtained in both processes.

TABLE 6

Molecular properties of the family of quinolines derivatives used.

| THQ Molecule | Log P (experimental) | Log P (theory) | TPSA | VM | PM | n ON | n OH NH |
|---|---|---|---|---|---|---|---|
| 3S | 0.434 + 0.005 | 4.314 | 22.196 | 237.394 | 249.313 | 2 | 0 |
| 4S | 2.662 + 0.006 | 4.706 | 12.892 | 228.409 | 233.314 | 1 | 0 |
| 55 | 1.973 + 0.003 | 3.334 | 38.915 | 223.137 | 234.302 | 2 | 2 |
| 56 | 0.293 + 0.002 | 2.909 | 38.915 | 206.576 | 220.275 | 2 | 2 |
| 9S | −0.214 + 0.003 | — | 12.892 | 229.734 | 298.183 | 1 | 0 |
| 12S | 2.584 + 0.009 | 4.682 | 12.892 | 228.409 | 233.314 | 1 | 0 |

Partition coefficient octanol/PBS buffer expressed as Log P;
TPSA: total surface of the polar areas;
VM: molecular volume;
PM: molecular weight;
n ON: hydrogen-accepting atoms;
n OH NH: hydrogen-donor atoms.

The calculation of total polar surface areas (TPSA), performed based on the individual contribution of each of the polar groups of these compounds (following the method of Ertl P., Rohde B., Selzer P. (2000), Fast calculation of molecular polar surface area as a sum of fragment-based contributions and its application to the prediction of drug transport properties, J. Med. Chem. 43: 3714-3717) shows that these drugs have TPSA values similar to other drugs having a good absorption and penetration of the BHE. The analysis of molecular properties, according to the "Rule of five 5" from Lipinski C. A., Lombardo L., Bominy B. W., Feeney P. J. (1997), Experimental and computational approaches to estimate solubility and permeability in drug discovery and development settings, Adv. Drug Delivery Rev. 23: 4-25, indicate that this drugs have structures that would help the penetration of BHE in the human being.

Purification of tau protein. To determine its purity, the tau protein was characterized by means of dotblots after its precipitation with ammonium sulphate salts and after the dialy-

TABLE 7

Tau protein concentrations obtained in the purification process.

| | Tau mass before the lyophilization | Tau mass before the lyophilization |
|---|---|---|
| htau preparation 1 | 0.16 | 1.70 |
| htau preparation 2 | 0.83 | 3.91 |
| btau preparation | 3.60 | 10.00 |

The concentrations were determined using the MicroBradford technique. After the purification the samples were lyophilized to obtain the right concentrations for the subsequent tests.

Figure 7:
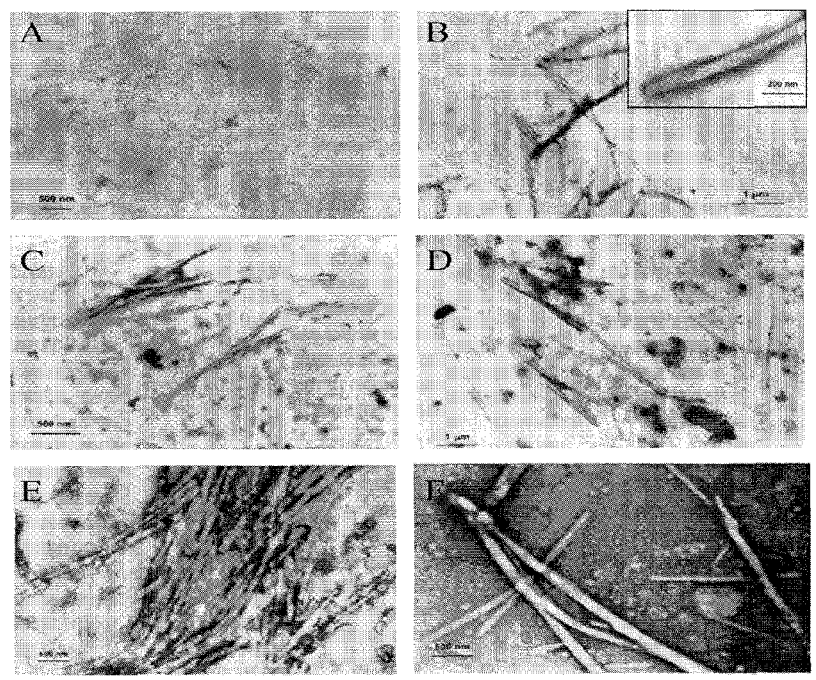
FIG. 7 shows the morphology studies of the tau filaments in presence and absence of quinolines. A) Electronic micrograph of the negative controls (tau without heparin and without quinolines). B) Micrograph of tau filaments obtained with heparin 200 µg/mL, without quinoline treatment (positive control). The insert illustrates a magnification of 30,000×. C) Electronic Micrograph of the incubation of tau with heparin and THQ 55 (see Table 1 hereinafter). D) Electronic micrograph of the incubation of tau with heparin and THQ 4S (see Table 1 hereinafter). E) Electronic micrograph of the purified PHFs from human brains through affinity columns. F) PHFs incubated with THQ 55 (see Table 1 hereinafter).

Proteic Aggregation Studies:

Effect of the quinolines in the aggregation of human tau. Electronic microscopy studies. After 7 days of incubating the protein at 37° C. under gentle agitation, tau aggregates were observed having morphologic characteristic similar to PHFs. This was achieved for both tau isolated from bovine brains and that isolated from human brains (FIGS. 7a) and 7b)).

Figure 8:
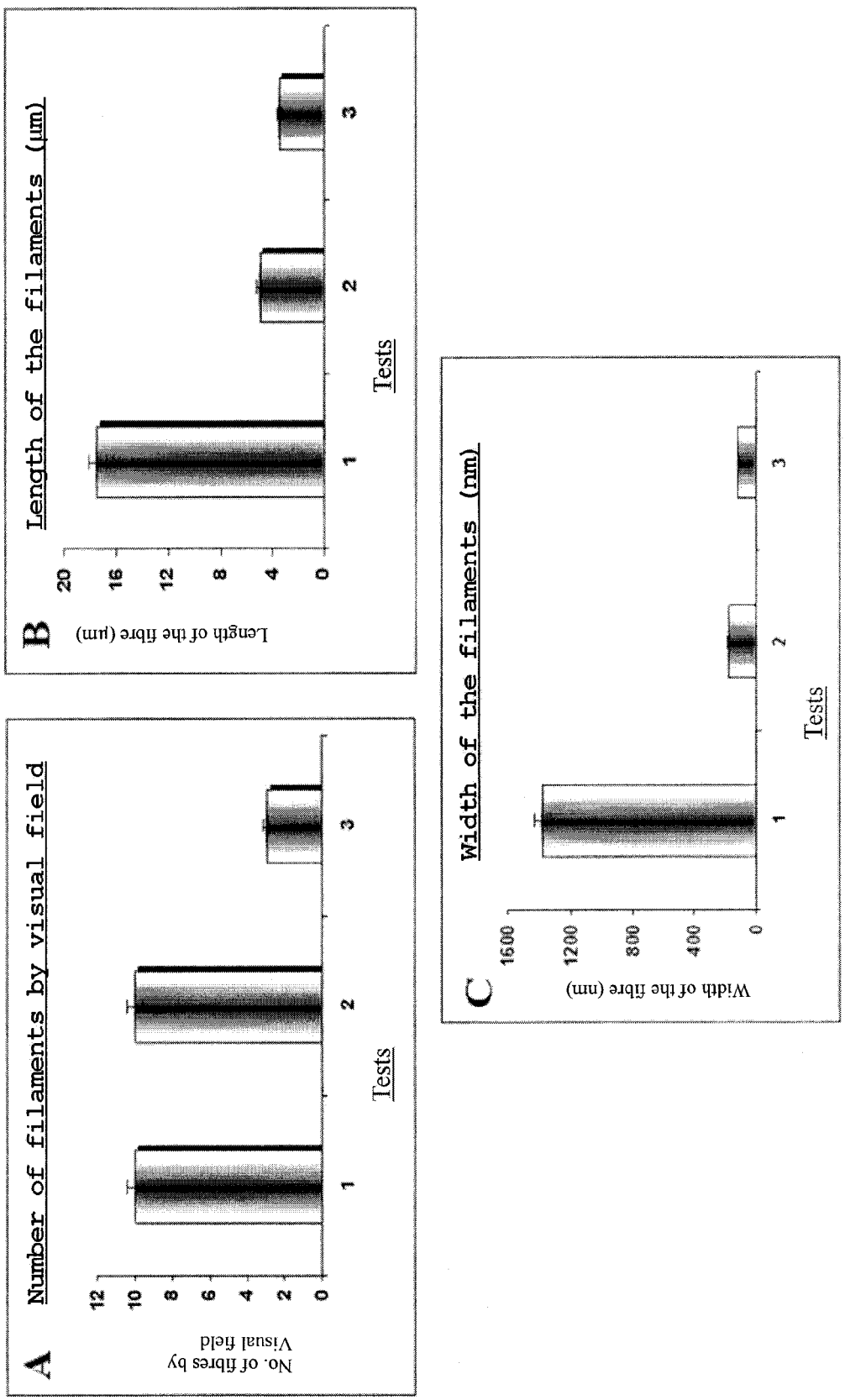
FIG. 8 shows that quinolines change the structure of the filaments resulting from the tau aggregation. A) Plot of the number of filaments per visual field after the treatment with the quinolines THQ4S and THQ55 (see Table 1 hereinafter); B) Length of the filaments (µm) after these treatments; and C) Width of the filaments obtained (nm). The aggregation studies show that these quinolines bind to the regulatory region of tau C-terminus and prevent its polymerization and affect the structure. (bar 1: polymerization control; bar 2 THQ 4S (see Table 1 hereinafter); bar 3 THQ 55 (see Table 1 hereinafter)).

Based on evidence that shows that a mutant tau having a deletion and without its C-terminus domain does not generate structures of the PHFs type (Jakes R, Novak M., Davison M., and Wischik M. (1991), Identification of 3 and 4 repeat tau isoformas within the PHF in Alzheimer's Disease, EMBO J. 10: 2725-2729), the aggregation studies that demonstrate the formation of PHFs indicate that the different quinolines would bind to the regulatory region of the C-terminus of tau. Thus, the quinolines would prevent its polymerization, also affecting the structure of the filaments (FIGS. 7c) and 7d)). The results also showed a decrease in both the number of filaments per field and in the length and width of each one of the filamentous structures (FIG. 8). When these quinolines (at a final concentration of 10 μM) were also incubated along with the PHFs purified from human brains, a decrease in the number of aggregates presented by the controls was observed. This result would indicate that together with preventing the polymerization, these quinolines would disaggregate the PHFs formed in patients affected by AD (FIGS. 7e) and 7f)).

Figure 9:
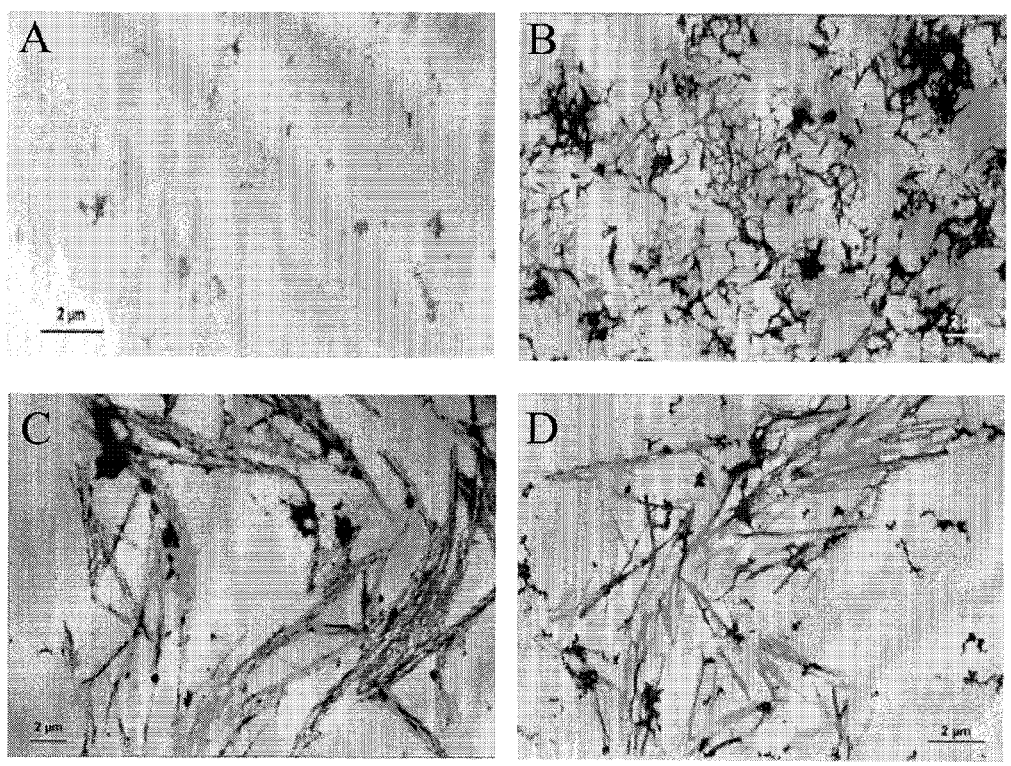
FIG. 9 shows the aggregation of the amyloid peptide in presence and absence of quinolines. A) Electronic micrograph of the controls obtained for the aggregates of Aβ 1-42 (Negative control). B) Polymerization of Aβ-42 by means of agitation at 37° C. for 7 days (positive control). C) Electronic micrograph of the incubation of Aβ 1-42 in presence of THQ 4S (see Table 1 hereinafter). D) Electronic micrograph of the incubation of Aβ 1-42 in presence of THQ 55 (see Table 1 hereinafter). All the samples are visualized at an amplification of 15,000×.

Effect of quinolines in the aggregation of Aβ 1-42 peptide. Electronic microscopy studies (ME). After 7 days of incubation at 37° C. under gentle agitation, aggregates of this peptide were obtained having the form of amyloid fibres (FIG. 9).

Figure 10:
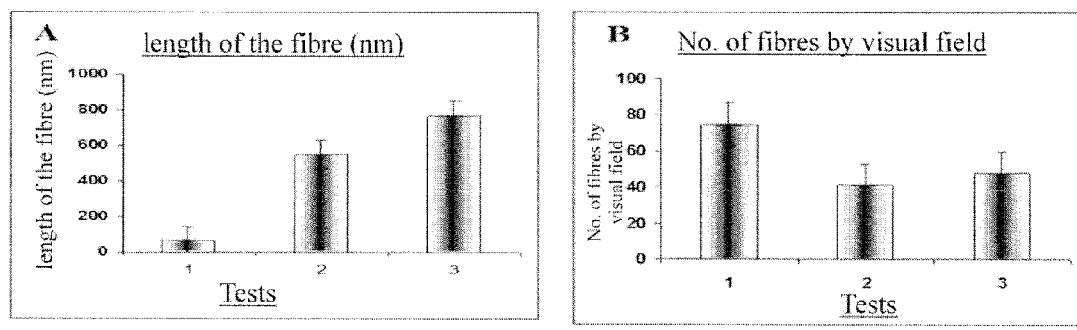
FIG. 10 shows that the quinolines slightly change the structure of the Aβ-42 filaments. A) Length of the filaments (µm) after the treatments with the quinolines THQ4S (see Table 1 hereinafter) and THQ55 (bars 2 and 3) (see Table 1 hereinafter); bar 1 represents the polymerization of the control without quinoline. B) Number of filaments by visual field after the treatment with the quinolines THQ4S (see Table 1 hereinafter) and THQ55 (bars 2 and 3) (see Table 1 hereinafter); bar 1 represents the polymerization of the control without quinoline.

These aggregation studies showed that quinolines, as with tau aggregation, prevent the polymerization of the Aβ 1-42 peptide and affect the structure of the filaments. The results show a decrease in the number of filaments per visual field, but an increase in the length of the fibres (FIG. 10). This is an interesting observation that is important to emphasize because it differentiates the effects of the quinolines over the tau and Aβ 1-42 aggregates. This sedimentation test (Maccioni R. B. and Seeds N. W. (1978), Enhancement of tubulin assembly as monitored by a rapid filtration assay, Arch. Biochem. Biophys. 185 (1): 262-71) further shows that the total mass of aggregated amyloid would not substantially decrease, as opposed to the tau polymers, wherein apparently there is a decrease in the quantity of tau monomers that aggregate.

Besides analysing the structural changes of the tau filaments obtained in the presence and absence of quinolines, it is also of interest to quantify the effect of these molecules in said aggregates. Consequently, sedimentation tests were carried out (Maccioni R. B., Vera J. C., Dominguez J., Ávila J. (1989), A discrete repeated sequence defines a tubulin binding domain on microtubule-associated protein tau, Arch. Biochem. Biophys. 275 (2): 568-79) as well as turbidimetric tests of the tau polymers in the absence and in presence of quinolines, analyzing the amount of tau polymerized at different concentrations of the drug.

Effect of the Quinolines in Tau Aggregation. Turbidimetric Studies.

Figure 11:
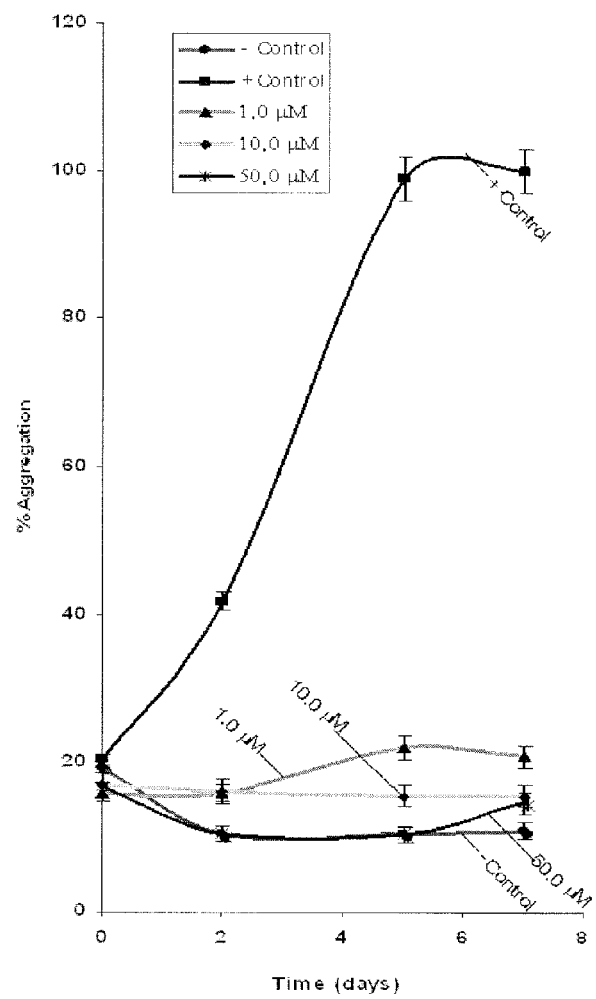
FIG. 11 shows the turbidimetric study for tau aggregation in absence and presence of quinolines at different concentrations. The lines are presented coloured for the different situations: + control (green); − control (red); sample in study plus THQ55 (see Table 1 hereinafter) at a concentration of 1.0 μM (q1 in yellow); sample in study plus THQ55 (see Table 1 hereinafter) at a concentration of 10 μM (q10 in blue); sample in study plus THQ55 (see Table 1 hereinafter) at a concentration of 50 μM (q50 in light blue); sample in study plus Astemizole at a concentration of 10 μM (Ast 10 in brown).

The inhibition of the aggregation of the tau protein is an important aspect of a potential therapeutic compound for the treatment of AD. THQ 55 quinoline THQ 55 (see Table 1) is used for this purpose. Said drug showed a high capacity to inhibit tau aggregation, a fact that was verified by measuring the absorbance at λ 340 (FIG. 11), that showed that at very low concentrations the drug has a potential effect over the aggregation.

Effect of the Quinolines in Tau Aggregation. Sedimentation Studies:

After 7 days of incubation at 37° C. under gentle agitation, the concentration of sedimented protein in the presence and absence of quinolines, and measured at λ 280 nm, showed as result a pronounced inhibitory effect of THQ 55 (see Table 1) over the auto-aggregation of tau protein in in-vitro tests.

This inhibitory effect is even more pronounced at concentrations of THQ 55 (see Table 1) higher than 10 μM. The concentrations of the tau polymers obtained in the sedimentation are indicated in Table 8.

TABLE 8

Sedimentation study for tau aggregation in the absence and in presence of quinolines.

| Samples | Tau polymer concentration (mg/mL) |
|---|---|
| +Control | 3.00 + 0.005 |
| −Control | 1.38 + 0.003 |
| Tau + THQ 55 (see Table 1) 1.0 μM | 2.72 + 0.002 |
| Tau + THQ 55 (see Table 1) 10.0 μM | 2.43 + 0.003 |
| Tau + THQ 55 (see Table 1) 50.0 μM | 0.79 + 0.004 |
| Ast 10 | 2.84 + 0.002 |

As positive control a solution containing tau, and heparin was used, and as a negative control only tau and water were used, while the samples under study contained tau protein, heparin and quinoline THQ 55 (see Table 1) at different concentrations between 1.0 and 50 μM. The other aggregation control contains tau, heparin and Astemizol (AST) at a concentration of 10 μM.

Figure 12:
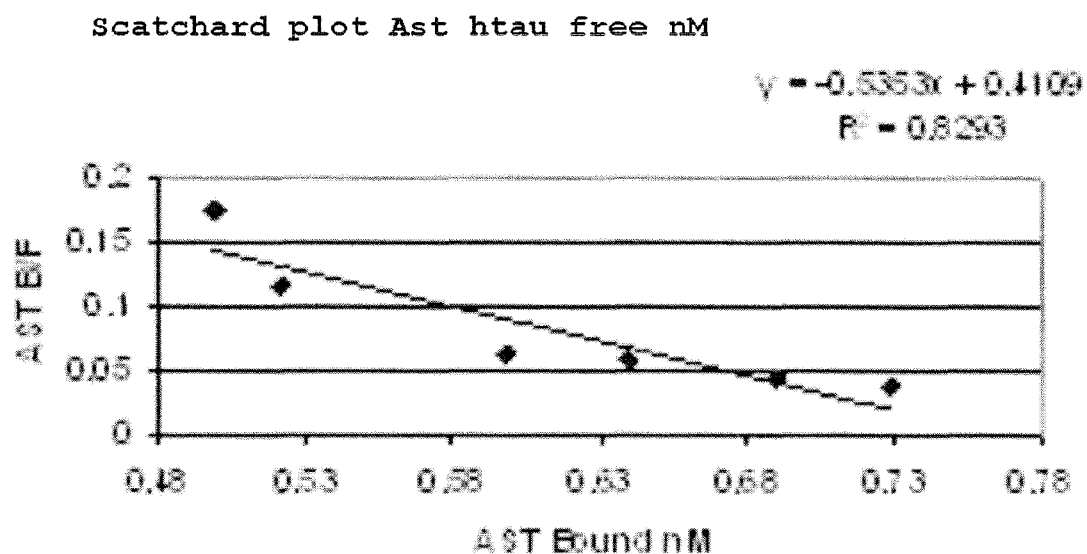
FIG. 12 is a Scatchard graphic for $^3$H-AST. These saturation studies carried out with tau filaments induced with heparin show that $^3$H-AST binds with a high affinity to tau.

Interaction of quinolines with tau and displacement tests with $^3$H-AST in-vitro. Based on the characterization of the tau-benzimidazoles system, the protein-ligand interaction parameters were studied. The results are shown in FIG. 12 and Table 9 and indicate that Astemizol binds with high affinity to tau filaments. This phenomenon is repeated when comparing the affinity for tau filaments induced in-vitro and for isolated filaments coming from AD brains (Rojo L., Avila M., Chandia M., and Maccioni R. B. (2007), 18F Lansoprazole as PET radiotracer, Chemical and biological studies towards the development of a New PET Radiotracer, International Conference on Clinical PET and Molecular Nuclear Medicine, 10-14 November, Bangkok).

Figure 13:
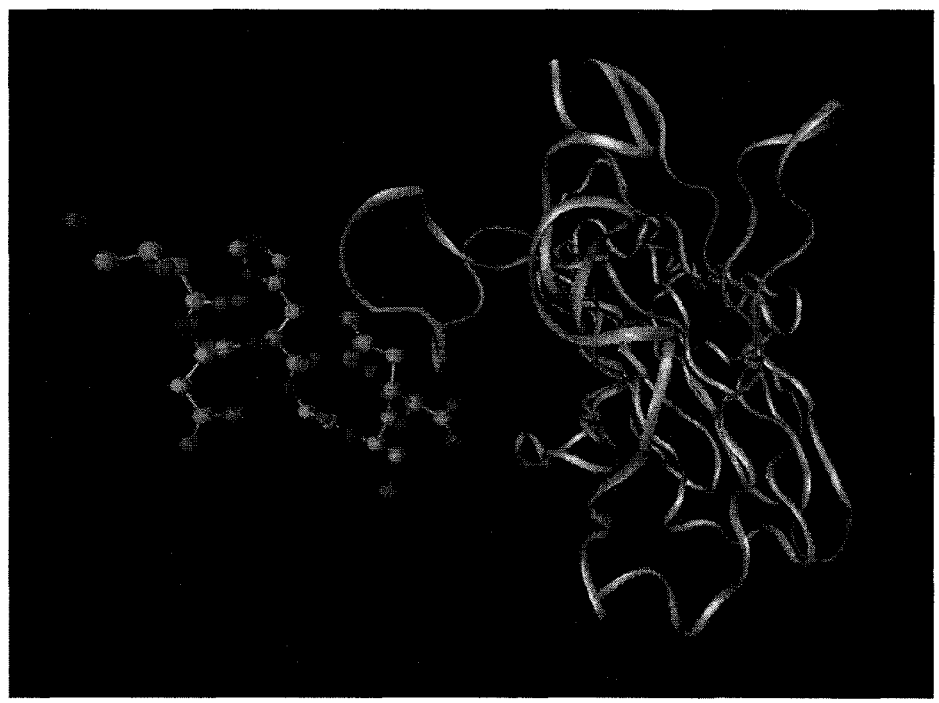
FIG. 13 shows the structure of the monoclonal antibody MN423 (light blue coloured ribbon) with the structural nucleus of tau C-terminus involved in the assembly of the PHFs, that pertains to the penta-peptide $^{387}$DHGAE$^{391}$ (coloured spheres).

In this context a $^3$H-AST displacement test was performed with quinolines to determinate its affinity with tau. The results presented in FIG. 13 reveal the affinity of quinolines for tau aggregates. It can be observed that the compound THQ 4S and THQ 55 (see Table 1) present very high Ki values, greater than 10 μM, indicating that these drugs do not displace the radioligand.

TABLE 9

Comparative analysis of the saturation data.

| Parameter | Human Tau (441 a.a.) | Human PHFs |
|---|---|---|
| Kd | 1.86 nM | 3.94 nM |
| Bmax | 5.7 pmol/nmol tau | 13.07 nM |
| Bmax/Kd index | 3.00 | 3.316 |

Kd, Bmáx, and Kb/Bmáx for $^3$H-AST, and tau aggregated forms.

Docking tests. As tau is a very fibrous protein with a large unstructured domain as statistic tangle ("random coiled") (Von Bergen M., Barghorn S., Biernat J., Mandelkow E. M., Mandelkow E. (2005), Tau aggregation is driven by a transition from random coil to beta sheet structure, Biochimica et Biophysica Acta. 1739: 158-166), a complete crystallization of this protein has not be achieved. Tau is not a protein with a totally regular structure. Consequently, up to date the crystalline structure of the whole protein is not known, and only the study performed by Novak M., Wischik C. M., Edwards P., Pannell R., Milstein C. (1989), Characterization of the first monoclonal antibody against the pronase resistant core of Alzheimer PHF, Prg. Clin. Biol. Res. 317: 755-61, describes the only known fragment, that consists of a penta-peptide $^{387}$DHGAE$^{391}$ located in the C-terminus domain, and that is involved in a regulatory region of the tau assembly in order to form the PHFs. This region contributes to the reactivity of the monoclonal antibody MN423 (FIG. 13) (Sevcik J., Skrabana R., Dvorsky R., Csokova N., Iqbal K., Novak M. (2007), X-ray structure of the PHF core C-terminus: insight into the folding of the intrinsically disordered protein tau in Alzheimer's disease, FEBS Lett. 581 (30): 5872-5878). Thus, on this basis, modelling was effected with this tau fragment, as it is exposed in the paired filaments of the protein as described by Novak M., Wischik C. M., Edwards P., Pannell R., Milstein C. (1989), Characterization of the first monoclonal antibody against the pronase resistant core of Alzheimer PHF, Prg. Clin. Biol. Res. 317: 755-61; and Skrabana R., Skrabanova M., Csokova N., Sevcik J., Novak M. (2006), Intrinsically disordered tau protein in Alzheimer's tangles: a coincidence or a rule?, Bratisi. Lek Listy. 107 (9-10): 354-8.

Figure 14:
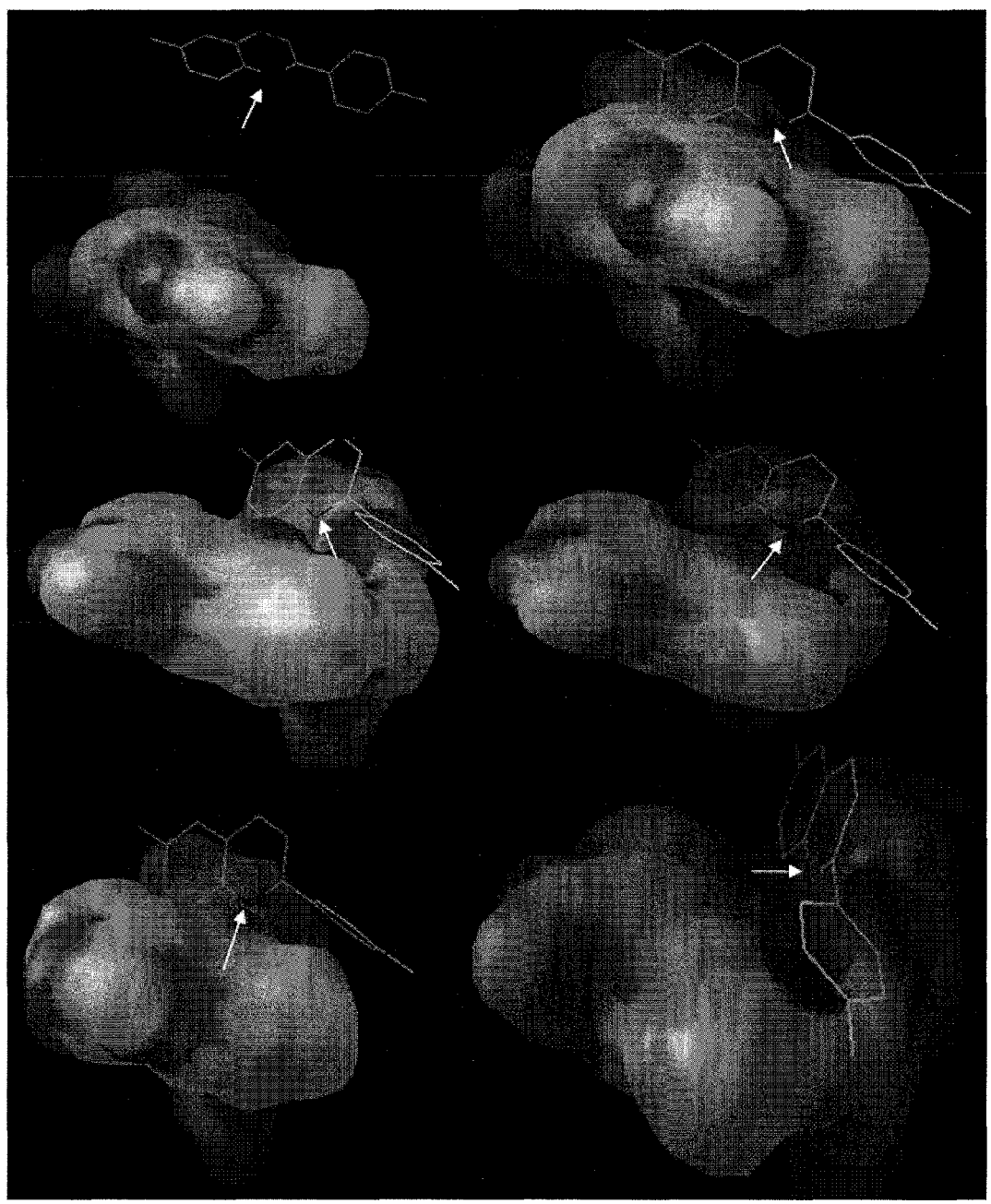
FIG. 14 shows the predictive bio-computerized analysis for 6 of the preferred configurations of the interaction of the penta-peptide pertaining to the PHF-tau C-terminus, with the THQ 4S (see Table 1 hereinafter), modelled by the Autodock® software. The white arrows indicate the position of N in the quinoline.

To complement this analysis, docking computing studies were performed employing the software Autodock III® using this known to date crystallographic structure for tau protein or fragments thereof. Docking studies were carried out, obtaining an approximation of the algorithms that enable the prediction of the type of more stable interaction produced between the quinolines and the tau protein. The docking between this penta-peptide and the THQ 4S quinoline (see Table 1), showed as result the most probable interactions (FIG. 14) with its respective docking energies that range from −4.5 to −4,47 Kcal/mol.

Table 10 summarizes the results obtained from the biocomputing analysis of the docking for THQ 4S (see Table 1) and the fragment resistant to pronasa PHF-tau-$^{387}$DHGAE$^{391}$ from which the crystalline structure is perfectly known. Thus, the binding energies described in this Table are compared to those obtained by the same software for drugs with a high affinity such as the metabotropic glutamate receptor (mGluR) (Yanamala N., Tirupula K. C. and Klein-Seetharaman J. (2008), Preferential binding of allosteric modulators to active and inactive conformational states of metabotropic glutamate receptors, BMC Bioinformatics 9 (Suppl 1): S16). The more negative energy values seem to be more thermodynamically favourable if they are related in terms of free energy ($\Delta G$), indicating that this quinoline is similar to the tau $^{387}$DHGAe$^{391}$ fragment, thus suggesting that this fragment could be involved in its binding and anti-aggregation activity.

TABLE 10

"Docking" energy comparison.

| Receptor | Species | Ligand | Docking Energies (Kcal/mol) | Reference |
| --- | --- | --- | --- | --- |
| Tau fragment | Human | THQ 4S (ver Table 1) | −4.5 to −4.47 | Oral communication(*) |
| mGluR I | Human | R214127 | −7.34 | Yanamala N., Tirupula K.C. and Klein-Seetharaman J. (2008), Preferential binding of allosteric modulators to active and inactive conformational states of metabotropic glutamate receptors, BMC Bioinformatics 9 (Suppl 1): S16 |
| mGluR 5 | Human | MPEP | −7.77 | Yanamala N., Tirupula K.C. and Klein-Seetharaman J. (2008), Preferential binding of allosteric modulators to active and inactive conformational states of metabotropic glutamate receptors, BMC Bioinformatics 9 (Suppl 1): S16 |

Energy obtained for THQ 4S quinoline, compared with the docking energy obtained for a high affinity receptor.

As it was mentioned before the objectives of this invention are directed to the pursue of ligand molecules that bind to the polymerized tau protein, as potential blockers of tau aggregation before the formation of NFTs. Is in this way that it has been possible to establish the manner by which a family of different quinolines interact with the tau protein, and in this way, to obtain a biomedical projection within AD. This would be the first finding described up to date that accomplishes identification of a new family of molecules that bind tau and at the same time interferes with its pathological auto-assembly in the path to neuro-degeneration. The study has been carried out essentially in in-vitro models, and according to the results achieved, it can be concluded that these quinolines would be candidates for blocking tau aggregation in its polymerized PHFs form.

Fluorescence tests. This study was directed to the determination of the affinity of quinolines for the tau protein and its aggregates, and to corroborate what has been proposed before by other authors (Rojo L., Avila M., Chandia M., and Maccioni R. B. (2007), 18F Lansoprazole as PET radiotracer, Chemical and biological studies towards the development of a New PET Radiotracer, International Conference on Clinical PET and Molecular Nuclear Medicine, 10-14 November, Bangkok; Okamura N., Suemoto T., Furumoto S., Suzuki. M., Shimadzu H., Akatsu H., Yamamoto T., Fujiwara H., Nemoto M., Maruyama M., Arai H., Yanai K., Sawada T., Kudo Y. (2005), Quinoline and bencimidazole derivatives: candidate probes for in vivo imaging of tau pathology in Alzheimer's disease, J. Neurosci. 25: 10857-10862). To this end fluorescence tests were performed, but the emission pattern of these compounds was found to be too low and very high concentrations of the drugs were needed to obtain a signal. Consequently and in accordance with the quinolines quantities needed to obtain a signal, this binding test could not be considered, because the quantity of protein needed for the binding with quinoline is too high.

Determination of the octano/water Log P partition coefficient. According to the development of this invention, one of the first properties analysed was whether these molecules, the quinolines, could cross the hemato-encephalic barrier and thus reach the brain. These molecules presented a relatively high liposolubility. The correlation between quinoline liposolubility and the capacity to cross the hemato-encephalic barrier (BHE) was optimal for three out of six compounds. The molecular properties analysis revealed that quinolines have properties similar to other drugs that cross the BHE. The result is a positive one as demonstrated throughout this description and suggests that these molecules could cross the BHE according to in-vitro model studies. In this context, the compounds must fulfil certain requirements to be of interest in a potential pharmacological application at a neural level: (1) they must be highly lipophilic and have the capacity to cross the hemato-encephalic barrier (BHE); (2) act at a low concentration and remain a short time in the brain tissue; (3) interact with the tau protein and its aggregates; and (4) have a low non-specific binding. In this way these drugs could come to exert a direct effect in the brain regions in persons suffering from AD. The quinolines herein described completely fulfil these requisites, namely, present the property of being highly lipophilic, interact with tau and exert their action by blocking their auto-aggregation in pathological polymers, such as PHFs. We consider this is a mayor finding, because to date no molecules fulfilling this properties have been described.

One of the first tests was to establish the liposolubility expressed as Log P. Our results show that the liposolubility of the THQ 4S, THQ 55 and THQ 12S compound (see Table 1) is optimal and make them serious candidates to cross the BHE. According to other physico-chemical and pharmacokinetic properties presented in Table 2, these quinolines have TPSA values are similar to other drugs that have a good absorption and penetration of the hemato-encephalic barrier. According to the "Rule of the five 5" of Lipinski C. A., Lombardo L., Bominy B. W., Feeney P. J. (1997), Experimental and computational approaches to estimate solubility and permeability in drug discovery and development settings, Adv. Drug Delivery Rev. 23: 4-25, the analysis of the molecular properties indicates that this drugs have structures that promote the penetration of the BHE in the human being and could exert their action at brain level. An important information is that many drugs of clinical use employed as anti-malaria have in their structure the nucleus of quinolines. In this context their use in human beings is approved and for their pharmacological evaluation the pre-clinical phase studied could be avoided. On this basis and according to their molecular properties, THQ 4S and THQ 55 were used (see Table 1) for the biological tests. As another related information, it is known that the permeability of the neuronal membrane further represents an important factor to obtain images of the tau intra-cellular aggregates (Small G. W., Agdeppa E. D., Kepe V., Satyamurthy N., Huang S. C., Barrio I. R. (2002), In vivo brain imaging of tangle burden in humans, J. Mol. Neurosci. 19: 323-327), wherein the high liposolubility of this compounds is an advantage.

Tau protein purification. As for the purification of tau protein, this protein is resistant to acidic conditions, and thus tau was frequently purified using precipitation with perchloric acid (Farías G. A., Vial C., and Maccioni R. B. (1992), Specific macromolecular interactions between tau and the microtubule system, Molecula and Cellular Biochemistry 112: 81-88) in one of the last steps of the purification. Subsequently, and based in the divulgations of Farias G. A., Munoz J. P., Garrido J., Maccioni R. B., Tubulin, actin, and tau protein interactions and the study of their macromolecular assemblies, (2002) J. Cell Biochem. 85: 315-324, the use of ammonium sulphate was introduced as a variant, thus allowing the concentration of tau with a slight increment in its purity. It is worth mentioning that the critical step in tau purification is based in the correct use of the polymerisation and de-polymerisation cycles, as described originally by Maccioni R. B., Rivas C. I., Vera J. C. (1988), Differential interaction of synthetic peptides from the carboxyl-terminal regulatory domain of tubulin with microtubule-associated proteins, EMBO J. 7 (7):1957-63).

Proteic aggregation studies. One of the most important studies is the visualization by which of these drugs block the polymerisation of tau protein. The results show a clear inhibition of the tau protein in its aggregated PHFs form, because the incubation of quinolines with the protein decreased both the number of filaments by visual field and the length and width of these filamentous structures. As a comparison, the same tests was performed with a human recombinant tau protein, obtaining the same results, but in this protein the number of aggregates was lower, because the recombinant protein is not phosphorylated and the number of PHFs to incubate with heparin is depleted. The quinolines decreased 5 times the length and 10 times the width of the tau filaments formed in-vitro. To prove that these drugs have a higher affinity for tau protein that for Aβ aggregates, the same tests as before were performed, revealing that the quinolines decrease the number of amyloid aggregates, but increase the length of the fibbers. The quinolines decreased the number of fibres but increase their length, suggesting that it would be related with a re-distribution of the masses and not an impediment of the aggregation.

This is an interesting observation that is important to emphasize due to the difference of the quinoline effects over the tau and Aβ 1-42 aggregates, indicating that the total amyloid aggregate mass would not decrease substantially, instead it would redistribute, as opposed to the tau polymers, wherein there is a decrease in the quantity of tau monomers that aggregate, as it is described hereinafter.

Turbidimetric and sedimentation assays. The Electronic Microscopy data were confirmed by means of sedimentation tests as well as turbidimetric tests, revealing an important inhibitory effect for THQ 55 (see Table 1) over the auto-aggregation of tau protein in in-vitro assays. A solid demonstration of the capacity of these quinolines to affect tau auto-aggregation was obtained by means of turbidimetric tests, followed by sedimentation of the tau polymers in presence of increasing concentration of the quinoline (THQ55, see Table 1). Thus, in a complementary manner to the precision microscopy, the sedimentation and turbidimetric tests, allowed to directly confirm the capacity of these drugs to prevent the tau aggregation. This inhibitory effect was even more important at THQ 55 concentrations (see Table 1) higher than 10 μM (see FIG. 10 and Table 8). These results suggest that this quinoline stands as a potential candidate to be a tau anti-aggregation agent, which would have an enormous relevance as therapeutic approach towards the control of neurofibrillary tangles in Alzheimer's disease.

On the other hand, it is worth mentioning that many small molecules that have been used as in-vitro inhibitors of amyloid polymerization contain aromatic rings in their structure. These inhibitors include Congo Red for β-amyloid, and anthraquinone, and porphyrines for tau (Pickhardt M., Gazova Z., von Bergen M., Khilistunova I., Wang Y., Hascher A., Mandelkow E. M., Biernat J. and Mandelkow E. (2005), Anthraquinones inhibit tau aggregation and dissolve paired helical filaments in vitro and in cells, J. Biol. Chem. 280: 3628-3635; Inouye H., Sharma D., Goux W. J. and Kirschner D. A. (2006), Structure of core domain of fibril-forming PHF/tau fragment, Biophys. J. 90: 1774-1789). As a difference from the anthraquinones and porphyrines, the quinolines are serious candidates towards a tau anti-aggregation therapy, because these cross BHE in addition to blocking tau aggregation at a low concentration, and even more, its use in patients has already been approved, unlike porphyrines and anthraquinones. Previous electronic microscopy and X ray diffraction studies performed on tau protein analogues have demonstrated that only 3 residues that conform the β foil could be involved in the polymerisation of filamentous forms of PHFs (Inouye H., Sharma D., Goux W. J. and Kirschner D. A. (2006), Structure of core domain of fibril-forming PHF/tau fragment, Biophys. J. 90: 1774-1789), this in accord with other studies that indicate that these interactions are established through H bridges or aromatic residues between small peptides (Gazit E. (2002), A possible role for π-stacking in the self-assembly of amyloids fibrils, FASEB J. 16: 77-83; Makin O. S., Atkins E., Sirkoski P., Johanson J. and Serpell L. C. (2005), Molecular basis for amyloid fibril formation and stability, Proc. Natl. Acad. Sci. USA 102: 315-320). This type of interaction could be used as a reasonable target to interfere with the fibre formation or to destroy the already formed fibre. Said studies are confirmed with the results obtained in the experiments of the invention, because the quinolines comprise 2 aromatic rings, very similar to naphthalene, but with one N in position 1. Another study performed by Inouye H., and Kischner D. A. (1991), Folding and function of the myelin proteins from primary sequence data, J. Neurosc. Res. 28: 1-17, to a tau domain located in the C-terminus end, that consists in a small peptide involved in the nucleation and polymerization in PHFs, indicates a possible interaction between tyrosines, thus suggesting that the inhibitors could bind to aromatic residues by means of interactions (Hunter C. A., Sanders J. K. M. (1990), The nature of π-π interactions, J. Am. Chem. Soc. 112: 5525-5534).

Displacement in-vitro studies with $^3$H-AST. Based on the fact that benzimidazole derivatives specifically and with high affinity bind tau protein gna NFTs (Rojo L., Avila M., Chandia M., and Maccioni R. B. (2007), 18F Lansoprazole as PET radiotracer, Chemical and biological studies towards the development of a New PET Radiotracer, International Conference on Clinical PET and Molecular Nuclear Medicine, 10-14 November, Bangkok; Okamura N., Suemoto T., Furumoto S., Suzuki M., Shimadzu H., Akatsu H., Yamamoto T., Fujiwara H., Nemoto M., Maruyama M., Arai H., Yanai K., Sawada T., Kudo Y. (2005), Quinoline and bencimidazole derivatives: candidate probes for in vivo imaging of tau pathology in Alzheimer's disease, J. Neurosci. 25: 10857-10862), suggested the possibility that quinolines could displace this interaction based on the similarity of their structure in the nucleus of the benzene ring and the N in position 1 of the benzimidazole ring. In this way it could displace the benzimidazole and bind to the aggregates of tau protein in-vitro. For this purpose H$^3$-AST is used, and the results show that the inhibition constants (Ki) obtained are very high (greater than 10 μM), indicating that these drugs do not displace the radioligand, so that the only option to obtain the affinity of these compounds for the protein would be to use a radio-labelled quinoline, which could not be commercially obtained. As a result, this experiment showed that the two quinolines do not have the capacity to displace the benzimidazoles used, thus suggesting that due to the very high Ki that these quinolines have, their affinity for tau is lower than benzimidazole, or else that in both molecules the interaction sites with the tau protein are different, an aspect this that should be investigated.

Docking tests. In this context, "docking" tests were performed to predict the form of interaction between the quinolines and tau protein. To perform these studies it was necessary to obtain a crystallized tau protein fragment. This is a key aspect because if the crystalline structure of the protein does not exist, the docking can not be done. Studies carried out by Glabe C. G. (Glabe C. G. (2004), Conformation dependent antibodies target diseases of protein misfolding, Trends Biochem. Sci. 29: 542-547), indicate that the tertiary structure of monoclonal antibodies is an essential tool for the investigation of the pathological assembly mechanisms of intrinsically disordered proteins (IDPs), as in the case of tau. Previous studies performed by Csokova (Csókova N, Skrabana R, Urbániková L, Kovácech B, Popov A, Sevcík J, Novák M. (2006), Preparation, crystallization and preliminary X-ray analysis of the Fab fragment of monoclonal antibody MN423, revealing the structural aspects of Alzheimer's paired helical filaments, Protein Pept Lett. 13:941-4) found that the MN-423 monoclonal antibody specifically binds to a PHF/tau structural nucleus, that consists of a sequence of 93-95 amino acids of the tau C-terminus resistant to pronase. Using this tau sequence (amino acids 306-391), the inventors carried out the crystallization of the protein for 3 months, wherein the detailed analysis showed that a penta-peptide $^{387}$DHGAE$^{391}$ that contributes to the reactivity of the antibody is involved in the assembly of the tau protein in PHFs structures, converting the known sequence in beta structure during the assembly of the filaments (Sevcik J., Skrabana R., Dvorsky R., Csokova N., Iqbal K., Novak M. (2007), X-ray structure of the PHF core C-terminus: insight into the folding of the intrinsically disordered protein tau in Alzheimer's disease, FEBS Lett. 581 (30): 5872-5878). Furthermore, it is important to add that this sequence is located in a zone that is highly preserved in tau, pertaining to the repetitive regions in the C-terminus.

Based on the information above and using this sequence, docking studies were carried out, which represent the first approximation based on mathematical models between the interaction of quinolines and tau. Through these studies it was established that these quinolines, specifically THQ 4S (see Table 1) have docking energies favourable for the interaction between these compounds and a fragment of tau protein. THQ 4S (see Table 1) was selected for these tests because of the advantages of its molecular properties and because it is more lipophilic than THQ 55 (see Table 1). The docking of THQ 55 (see Table 1) with this tau fragment is an aspect that remains to be investigated, even tough possibly the interaction energies of THQ 55 (see Table 1) may be even more negative that those of THQ 4S (see Table 1) because THQ (see Table 1) presents electron donor groups in the substituents that could influence the resonance of the aromatic rings in the quinoline and delocalize the electrons, thus leaving the N more negative and collaborating with the interaction with a cationic protein as in the case of tau. Besides, this is confirmed with an important information obtained from this approximation, namely that this N in the quinoline (FIG. 22, indicated with white arrows) interacts with an O that protrudes in the final end of the peptide, that constitutes a small cavity formed between the Ala and Glu ("pocket" structures). This nitrogen atom could be replacing one N in the Arg 106 of the MN-423 Aβ specific.

Even though the results obtained are relevant, the binding domain can not be precisely establish because the peptide is very small and it only provides an approximation of a possible interaction between tau and the quinolines.

Thus, the objective of this invention is directed mainly to the research of ligand molecules binding to polymerized tau, as potential blockers of tau aggregation before the NFTs formation. The precision microscopy studies, the sedimentation and turbidimetric tests, allowed to directly confirm the capacity of these drugs to prevent tau aggregation.

On the other hand, these molecules present a relatively high liposolubility and have molecular properties similar to other drugs that cross the BHE, by which they can eventually exert an action at brain level. From these results it is concluded that these quinolines and their derivatives can be used as potential inhibitor drugs of tau aggregation, in a probable therapeutic path for AD treatment.

The invention claimed is:

1. A method for inhibiting tau protein aggregation in an Alzheimer's patient, which comprises the administration of a quinoline derivative of the formula:

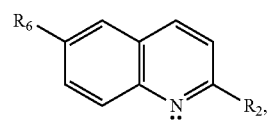

wherein $R_2$ is 2-(4-methylphenyl) and $R_6$ is methyl.

* * * * *